(12) United States Patent
Muramatsu

(10) Patent No.: US 10,738,326 B2
(45) Date of Patent: Aug. 11, 2020

(54) ADENO-ASSOCIATED VIRUS VECTOR FOR GENE TRANSFER TO NERVOUS SYSTEM CELLS

(75) Inventor: Shinichi Muramatsu, Tochigi (JP)

(73) Assignee: Jichi Medical University, Tochigi (JP)

( * ) Notice: Subject to any disclaimer, the term of this patent is extended or adjusted under 35 U.S.C. 154(b) by 0 days.

(21) Appl. No.: 13/881,956

(22) PCT Filed: Oct. 26, 2011

(86) PCT No.: PCT/JP2011/075240
§ 371 (c)(1),
(2), (4) Date: Apr. 26, 2013

(87) PCT Pub. No.: WO2012/057363
PCT Pub. Date: May 3, 2012

(65) Prior Publication Data
US 2013/0224836 A1    Aug. 29, 2013

(30) Foreign Application Priority Data

Oct. 27, 2010  (JP) ................................ 2010-240581

(51) Int. Cl.
| | | |
|---|---|---|
| *A61K 35/76* | (2015.01) | |
| *A61K 38/44* | (2006.01) | |
| *A61K 38/48* | (2006.01) | |
| *C12N 15/861* | (2006.01) | |
| *A61K 48/00* | (2006.01) | |
| *C12N 15/86* | (2006.01) | |
| *C12N 15/113* | (2010.01) | |
| *A61K 38/18* | (2006.01) | |

(52) U.S. Cl.
CPC .......... *C12N 15/861* (2013.01); *A61K 48/005* (2013.01); *C12N 15/86* (2013.01); *A61K 38/185* (2013.01); *A61K 38/1825* (2013.01); *A61K 38/1833* (2013.01); *A61K 38/44* (2013.01); *A61K 38/48* (2013.01); *C12N 15/1137* (2013.01); *C12N 2310/141* (2013.01); *C12N 2320/32* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 6,156,303 A | * | 12/2000 | Russell et al. ............... 424/93.2 |
| 2002/0086847 A1 | * | 7/2002 | Chain .......................... 514/44 |
| 2007/0036760 A1 | | 2/2007 | Wilson et al. |
| 2010/0240739 A1 | * | 9/2010 | Barkats ................. C12N 15/86 |
| | | | 514/44 R |

FOREIGN PATENT DOCUMENTS

| | | |
|---|---|---|
| JP | 2002-539098 A | 9/2002 |
| JP | 2005-501127 A | 1/2005 |
| JP | 2007-507223 A | 3/2007 |
| JP | 2007-524386 A | 8/2007 |
| WO | 1995028493 A1 | 10/1995 |
| WO | 2000/028061 A2 | 5/2000 |
| WO | 2000028061 A2 | 5/2000 |
| WO | 2003/018821 A2 | 3/2003 |
| WO | 2003093479 A1 | 11/2003 |
| WO | 2004/112727 A2 | 12/2004 |
| WO | 2007/001010 A1 | 1/2007 |
| WO | 2008124724 A1 | 10/2008 |
| WO | 2009043936 A1 | 4/2009 |
| WO | 2009140649 A2 | 11/2009 |

OTHER PUBLICATIONS

Nathanson et al. Preferential labeling of inhibitory and excitatory cortical neurons by endogenous tropism of adeno-associated virus and lentivirus vectors. Neuroscience. Jun. 30, 2009;161(2):441-50. Epub Mar. 24, 2009.*
Petrs-Silva et al. High-efficiency Transduction of the Mouse Retina by Tyrosine-mutant AAV Serotype Vectors. Molecular Therapy vol. 17 No. 3, 463-471 Mar. 2009.*
Gen Bank: M55300.1. Rat synapsin I gene, 5' end. http://www.ncbi.nlm.nih.gov/nucleotide/207142?report=genbank&log$=nuclalign&blast_rank=1&RID=SH7SHP1K01R.*
GenBank: AAS99284.1. capsid protein VP1 [Adeno-associated virus]. Jun. 24, 2004. http://www.ncbi.nlm.nih.gov/protein/46487845?report=genbank&log$=protalign&blast_rank=3&RID=SHGE6WB4014.*

(Continued)

*Primary Examiner* — Nianxiang Zou
(74) *Attorney, Agent, or Firm* — Morgan, Lewis & Bockius LLP

(57) ABSTRACT

The present invention provides a means for transferring a therapeutic gene of interest into a nervous system cell by a highly-efficient and simpler means. More specifically, the present invention provides a recombinant vector that uses an adeno-associated virus (AAV), a method for manufacturing the recombinant vector, and a method for using the recombinant vector. More specifically, recombinant adeno-associated virus virions, which are capable of passing through the brain-brain barrier, for transferring a therapeutic genes of interest into a nervous system cell in a highly-efficient manner, a drug composition containing the recombinant adeno-associated virus virions, a method for manufacturing the recombinant adeno-associated virus virions, and a kit or the like are provided.

16 Claims, 4 Drawing Sheets

Specification includes a Sequence Listing.

(56) References Cited

OTHER PUBLICATIONS

Gorbatyuk et al. In Vivo RNAi-Mediated a-Synuclein Silencing Induces Nigrostriatal Degeneration. Molecular Therapy, 2010, 18:1450-1457.*
Bosch et al. Long-term and significant correction of brain lesions in adult mucopolysaccharidosis type VII mice using recombinant AAV vectors. Mol Ther. Jan. 2000;1(1):63-70.*
GenBank: AF410461.1. Mus musculus RPE65 (Rpe65) mRNA, complete cds. May 17, 2005. http://www.ncbi.nlm.nih.gov/nuccore/AF410461.1.*
Chung et al. Recent advances in ocular gene therapy. Current Opinion in Ophthalmology 2009, 20:377-381.*
Martinez-Navarrete et al. Alpha-Synuclein gene expression profile in the retina of vertebrates. Molecular Vision 2007; 13:949-61.*
Ning et al. Amyloid-beta Deposits Lead to Retinal Degeneration in a Mouse Model of Alzheimer Disease. Invest Ophthalmol Vis Sci. 2008;49:5136-5143.*
GenBank: AAK76419.1. capsid protein VP1 [Cloning vector pAAV-RC]. Jul. 22, 2001.*
NP_049542.1. capsid protein [Adeno-associated virus-1] NCBI Reference Sequence: NP_049542.1 http://www.ncbi.nlm.nih.gov/protein/NP_049542.1. Dated Mar. 11, 2010.*
Kugler et al. Differential transgene expression in brain cells in vivo and in vitro from AAV-2 vectors with small transcriptional control units. Virology 311 (2003) 89-95.*
NP_049542.1. capsid protein [Adeno-associated virus-1]. Dated Mar. 11, 2010.*
GenBank: AAS99264.1. capsid protein VP1 [Adeno-associated virus 9]. Dated Jun. 24, 2004.*
Chen et al. Oligodendrocyte-Specific Gene Expression in Mouse Brain: Use of a Myelin-Forming Cell Type-Specific Promoter in an Adeno-Associated VirusJ. Neurosci. Res. 55:504-513, 1999.*
Hashimoto et al. A neural cell-type-specific expression system using recombinant adenovirus vectors. Hum Gene Ther. Jan. 20, 1996;7(2):149-58.*
Foust et al. Intravascular AAV9 preferentially targets neonatal neurons and adult astrocytes. Nature Biotechnology. 2009. 27: 59-65. (Year: 2009).*
GenBank: AAS99264.1. capsid protein VP1 [Adeno-associated virus 9]. Dated Jun. 24, 2004. (Year: 2004).*
NP_049542.1. capsid protein [Adeno-associated virus-1]. Mar. 11, 2010.*
Hashimoto et al. A Neural Cell-Type-Specific Expression System Using recombinant adenovirus vectors. Human Gene Therapy 7:149-158. 1996.*
Gray et al., "Directed Evolution of a Novel Adeno-associated Virus (AAV) Vector That Crosses the Seizure-compromised Blood-Brain Barrier (BBB)," American Society of Gene & Cell Therapy, 18(3): 570-578 (2010).
Nakai et al., "Unrestricted Hepatocyte Transduction with Adeno-Associated Virus Serotype 8 Vectors in Mice," Journal of Virology, 79(1): 214-224 (2005).
Foust et al., "Intravascular AAV9 preferentially targets neonatal neurons and adult astrocytes," Nature Biotechnology, 27(1): 59-65 (2009).
Duque et al., "Intravenous Administration of Self-complementary AAV9 Enables Transgene Delivery to Adult Motor Neurons," Molecular Therapy, 17(7): 1187-1196 (2009).
International Search Report issued in corresponding International Patent Application No. PCT/JP2011/075240 dated Dec. 13, 2011.
Report on the Assigned Study: Research Team of "Development of Innovative Therapy based on Pathological Condition of Amyotrophic Lateral Sclerosis", Mar. 2010, pp. 30-31.
Kevin D. F., et al., Nature Biotech., vol. 27, No. 1, Dec. 21, 2008, pp. 59-65.
Royo et al., Brain Res., Elsevir, Amsterdam, NL, vol. 1190, Nov. 17, 2007, pp. 15-22.
Sandra D. et al., Mol. Thera., vol. 17, No. 7, Jul. 1, 2009, pp. 1187-1196.
Zhong, L. et al., PNAS, vol. 105, No. 22, Jun. 3, 2008, pp. 7827-7832.
Chumping, Q., et al., Hum. Gene Thera., vol. 21, No. 10, Oct. 1, 2010, pp. 1343-1348.
M. Ariel Kauss et al., Hum. Gene Thera., vol. 21, No. 9. Sep. 1, 2010, pp. 1129-1136.
European Search Report of corresponding European Application No. 11836494.2, dated Feb. 24, 2014.
GenBank AAS99284.1, Jun. 24, 2004.
GenBank AAS99264.1, Jun. 24, 2004.

* cited by examiner

[FIG. 1]
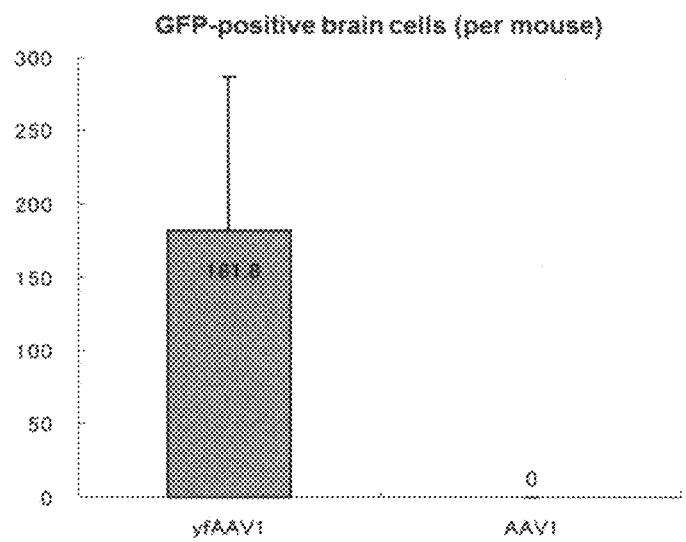
[FIG.2A]
A: yfAAV9-CAG-GFP
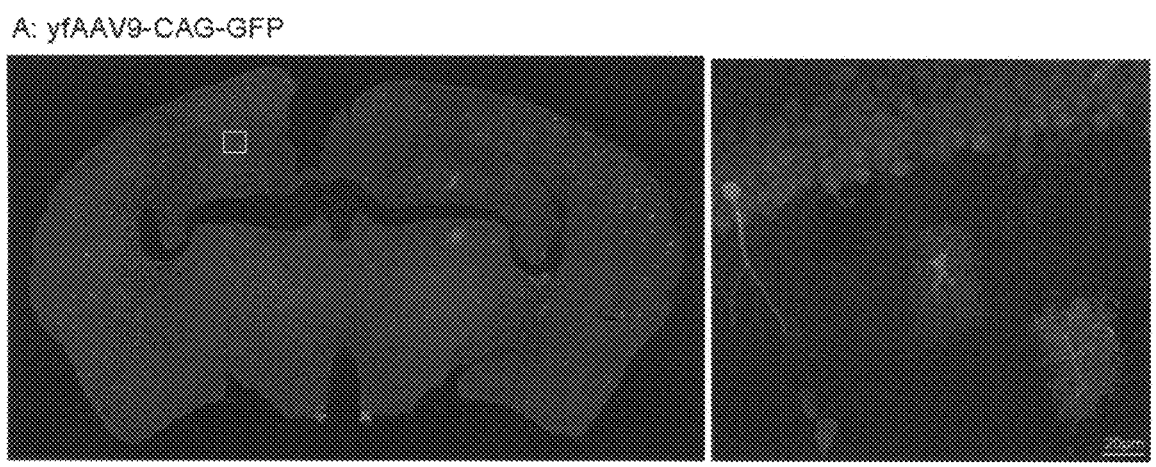
[FIG.2B]
B: yfAAV9-SynI-GFP
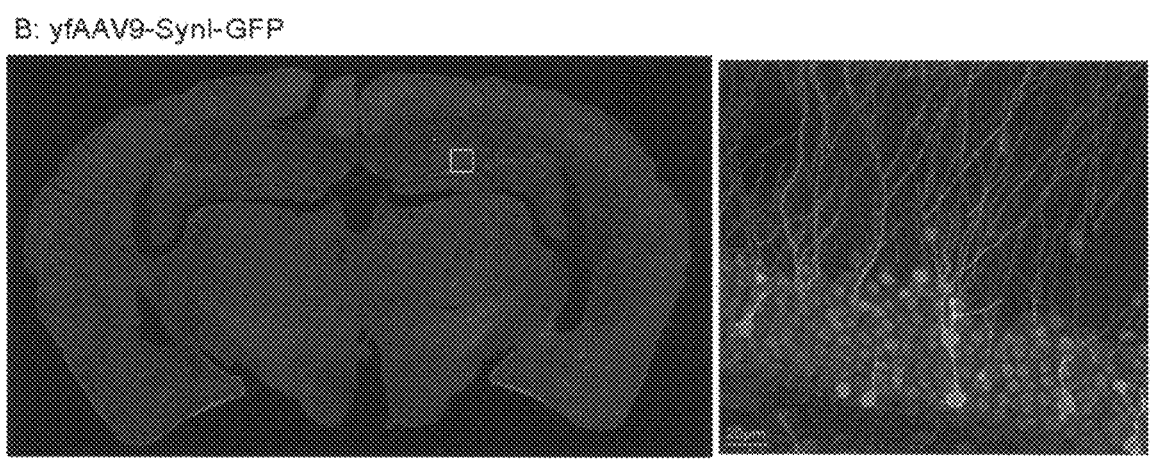

[FIG.2C]
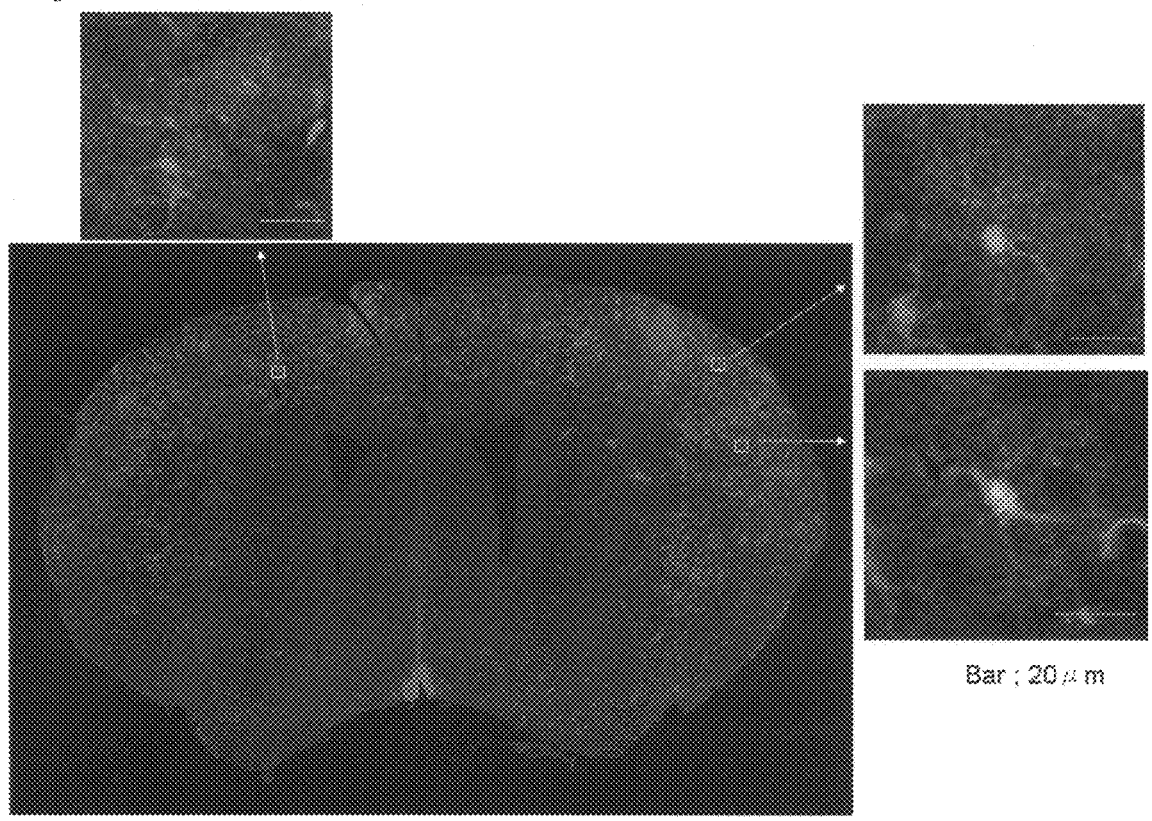
C: yfAAV9-MBP-GFP
Bar : 20 μm
[FIG.3]
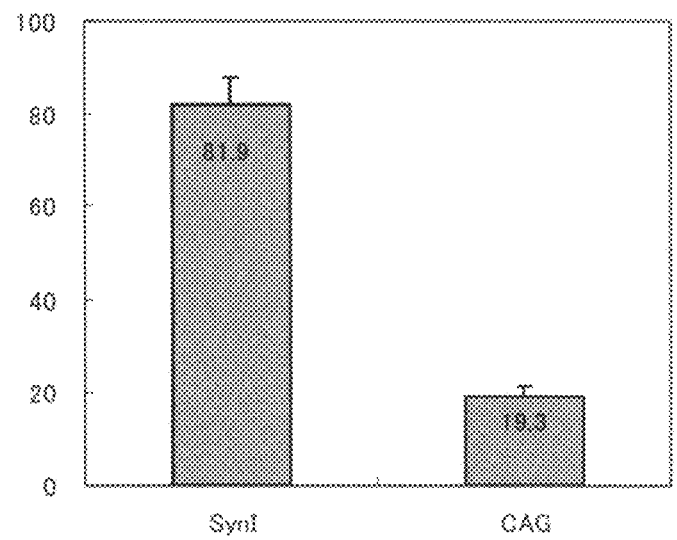
GFP-positive cells (per 0.04 mm³ cerebral cortex)

[FIG.4]
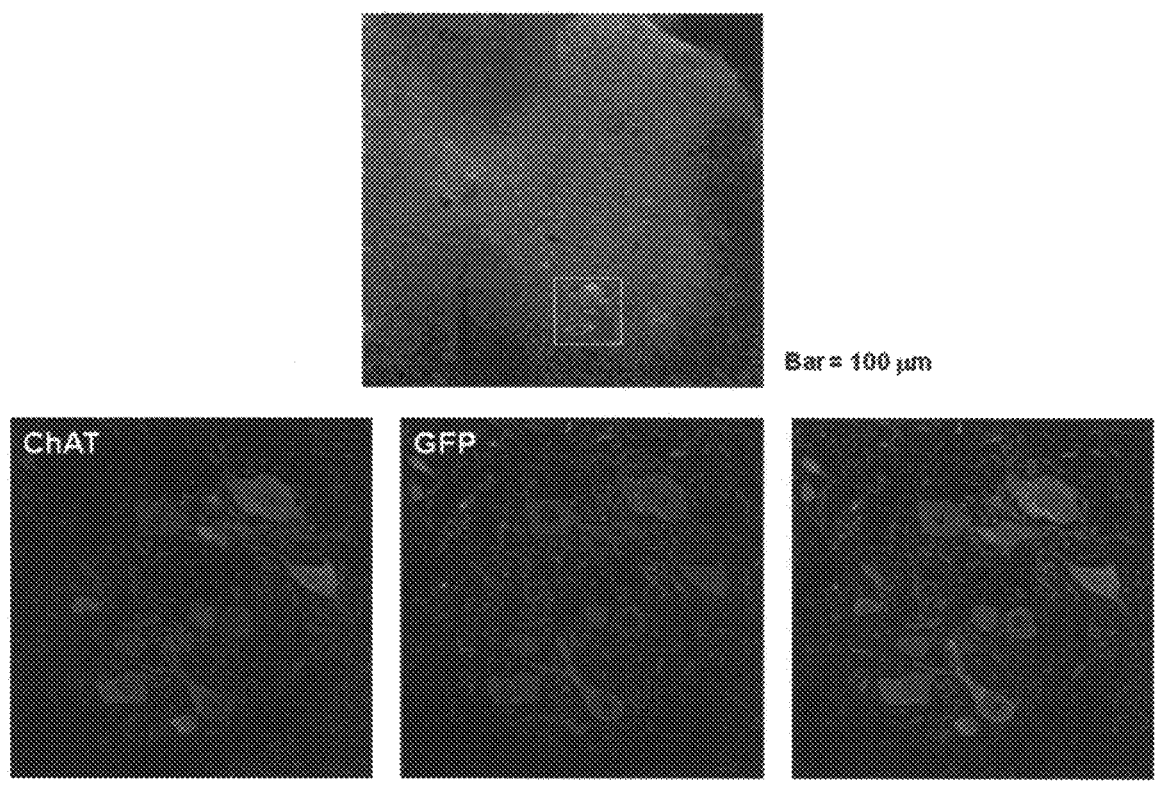

[FIG.5]
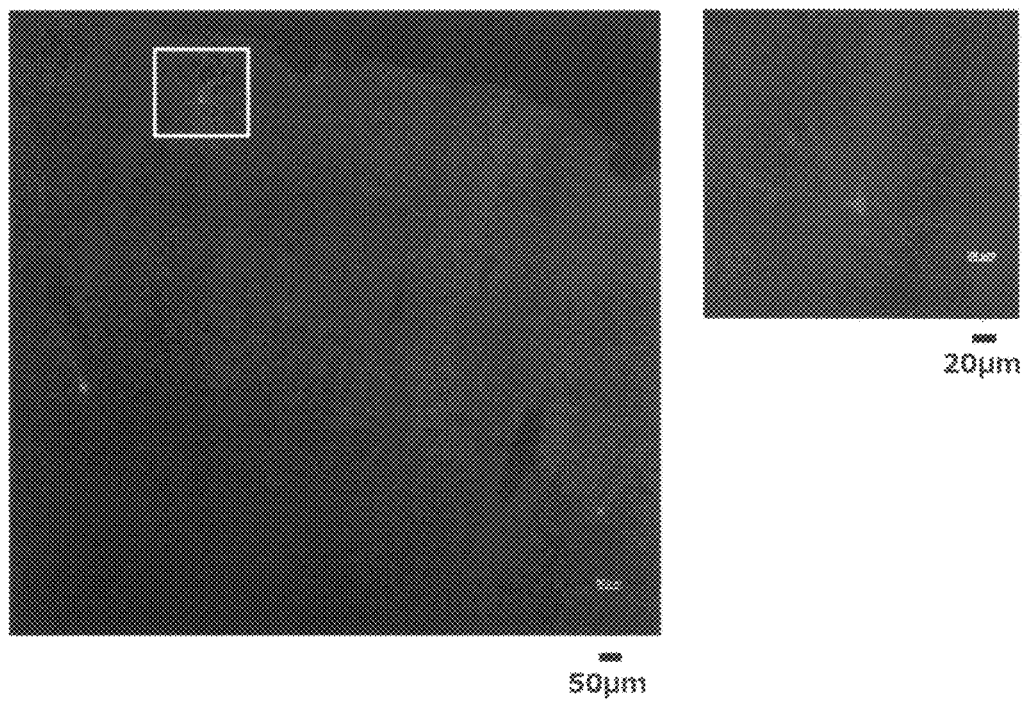
[FIG.6]
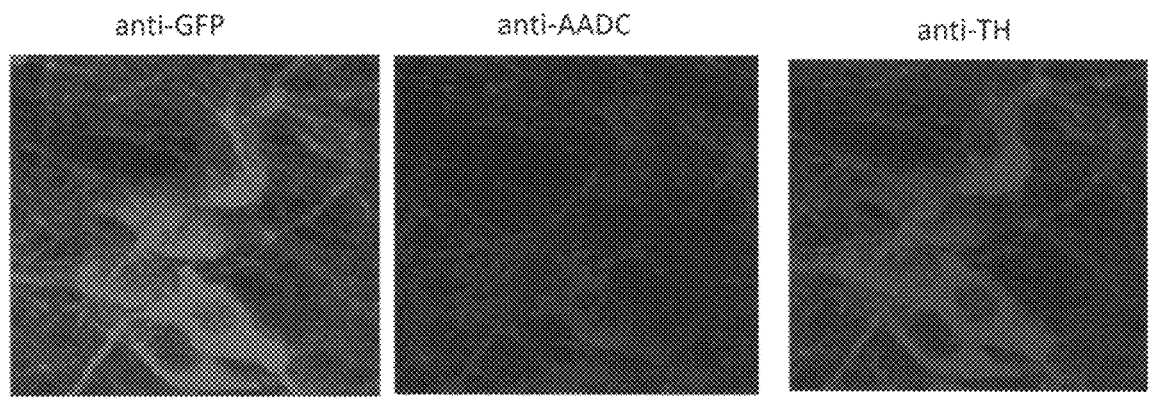
anti-GFP anti-AADC anti-TH

ADENO-ASSOCIATED VIRUS VECTOR FOR GENE TRANSFER TO NERVOUS SYSTEM CELLS

The file of this patent contains at least one drawing executed in color. Copies of this patent with color drawing(s) will be provided by the Office upon request and payment of the necessary fee.

SEQUENCE LISTING SUBMISSION VIA EFS-WEB

A computer readable text file, entitled "SequenceListing.txt," created on or about Apr. 25, 2013 with a file size of about 121 kb contains the sequence listing for this application and is hereby incorporated by reference in its entirety.

TECHNICAL FIELD

The present invention relates to a recombinant adeno-associated virus (rAAV) virion used for gene transfer. More specifically, the present invention relates to a recombinant adeno-associated virus (rAAV) virion, which is capable of passing through a blood-brain barrier for transferring a gene of interest into a nervous system cell with high efficiency, a composition comprising the same, and so on.

BACKGROUND ART

Central nervous system disorders have caused serious public health concerns. The number of patients in Japan with Alzheimer's disease alone, which results in cognitive dysfunction due to the degeneration and loss of nerve cells, is estimated to be more than 600,000. Currently, central nervous system disorders are treated mostly by systemic administration of therapeutic drugs. In systemic administration, however, drugs are usually incapable of passing through the blood-brain barrier and are often inefficient. Thus, many potentially useful therapeutic proteins, etc. cannot be administered systemically.

There are known methods for using an adeno-associated virus (AAV) as a vector derived from a virus for gene therapy (e.g., WO2003/018821, WO2003/053476, WO2007/001010, etc.). However, when gene transfer to a nervous system cell such as in the brain is attempted, it is necessary to consider problems including defensive functions such as the blood-brain barrier, etc., the transduction efficiency to nervous system cells, the expression efficiency, a safer route for administration, and the like.

Nakai H., et al. (Unrestricted hepatocyte transduction with adeno-associated virus serotype 8 vectors in mice. J. Virol. 2005 January; 79(1): 214-24) discloses an example of using a serotype 8 AAV vector AAV8-EF1α (-nlslacZ) expressing a LacZ gene marker with an EF1α promoter, for the purpose of gene transduction to hepatocytes.

Foust K. D., et al. (Intravascular AAV9 preferentially targets neonatal neurons and adult astrocytes. Nat. Biotechnol. 2009 January; 27(1): 59-65) discloses a self-complementary (sc) vector with the coat protein of serotype 9 AAV (AAV9) that expresses a green fluorescent protein (GFP) under the control of a chicken-β-actin hybrid promoter (CB). Duque S., et al. (Intravenous Administration of Self-complementary AAV9 Enables Transgene Delivery to Adult Motor Neurons. Mol. Ther. 2009 July; 17(7): 1187-96) also discloses a self-complementary vector (scAAV9-GFP) with a serotype 9 AAV (AAV9) capsid protein that expresses GFP under the control of the cytomegalovirus immediate-early promoter (CMV) (cf., Table 1 for the summary of the results).

Gene transfer to the brain (including neurons from neonates, astrocytes from adults, etc.) has been performed through intravascular administration of these recombinant AAV9 vectors. However, it is necessary to incorporate a reverse sequence to generate an sc type viral genome, a gene that can be incorporated into the viral genome becomes half as long as a non-sc type viral genome. Specifically, the length of the gene that can be incorporated in the sc type vector is limited to a length as small as 2 kb including the promoter and poly(A) region. By means of this limitation, therapeutic applications of recombinant viral vectors are limited as well.

As described above, various recombinant adeno-associated virus vectors have been produced. However, there are unknown vectors such recombinant AAV vectors that can make use of non-sc form AAV genomes that are capable of passing through the blood-brain barrier in a living subject and as associated with simple administration to enable efficient gene transfer especially to a nervous system cell in the brain, whereby a wider range of therapeutic applications can be expected.

PRIOR ART DOCUMENTS

Non-Patent Documents

[Non-Patent Document 1] Nakai H., et al. (J. Virol. 2005 January; 79(1): 214-24.)
[Non-Patent Document 2] Foust K. D., et al. (Nat. Biotechnol. 2009 January; 27(1): 59-65.)
[Non-Patent Document 3] Duque S., et al. (Mol. Ther. 2009 July; 17(7): 1187-96.)

DISCLOSURE OF THE INVENTION

Problems to be Solved by the Invention

Under the foregoing circumstances, it has been desired to develop a viral vector (virus virion) which can deliver a therapeutic gene of interest to a nerve cell located in brain, spinal cord, etc. of a living subject, especially a nerve cell in the brain, through a simpler administration route with high efficiency, and which can package a non-sc type viral genome to allow the gene of interest to be selected from a wider range of length.

Means for Solving the Problems

As a result of extensive studies, the present inventors have successfully achieved constructing a recombinant adeno-associated virus (rAAV) virion capable of transferring a gene to a nervous system cell with significantly high efficiency through peripheral administration to a subject by modifying a wild type capsid protein for usual single-stranded AAV, and by using the resultant configuration in combination with a recombinant AAV genome containing an oligodendrocyte-specific promoter or a synapsin I promoter, which is nervous system cell-specific.

More specifically, the present invention provides a recombinant adeno-associated virus (rAAV) virion which is capable of transferring a therapeutic gene to a nervous system cell in the brain, spinal cord, etc. of a living subject with high efficiency and is capable of passing through the blood-train barrier in addition to aspects such as a pharmaceutical composition comprising the same.

[1] A recombinant adeno-associated virus virion comprising:

(a) a capsomere which comprises a protein comprising an amino acid sequence having at least 90% identity to the amino acid sequence of SEQ ID NO: 2, 4 or 6, wherein at least one of surface-exposed tyrosine residues in the amino acid sequence is substituted with another amino acid residue, and the protein is capable of forming a virus virion, and (b) a polynucleotide packaged in said capsomere which comprises a nervous system cell-specific promoter sequence and a nucleotide sequence operably linked to the promoter sequence.

[1a] The virus virion according to [1], wherein the nervous system cell-specific promoter sequence is derived from a nerve cell, glial cell or oligodendrocyte.

[2] The virus virion according to [1], wherein the protein comprises an amino acid sequence in which at least the tyrosine residue at position 445 in SEQ ID NO: 2, the tyrosine residue at position 444 in SEQ ID NO: 4 or the tyrosine residue at position 446 in SEQ ID NO: 6 is substituted.

[3] The virus virion according to claim 1 or 2, wherein the tyrosine residue is substituted with phenylalanine residue.

[4] The virus virion according to any one of [1] to [3], wherein the protein comprises:

the amino acid sequence of SEQ ID NO: 8, 10 or 12, or an amino acid sequence in which 1 to several amino acids are deleted, substituted, inserted and/or added at positions other than positions 444 to 446 in the amino acid sequence of SEQ ID NO: 8, 10 or 12; and wherein the protein is capable of forming a virus virion.

[5] The virus virion according to any one of [1] to [4], wherein the 5' and 3' ends of the polynucleotide contain the 5' and 3' end-inverted terminal repeat (ITR) sequences derived, respectively, from AAV1, AAV2, AAV3 or AAV4.

[6] The virus virion according to any one of [1] to [5], wherein the 5' and 3' ends of the polynucleotide contain the nucleotide sequences of SEQ ID NO: 13 and SEQ ID NO: 14, respectively.

[7] The virus virion according to any one of [1] to [5], wherein the polynucleotide has a full length of approximately 2 to 6 kb and is a single stranded DNA which is a sense strand or an antisense strand.

[8] The virus virion according to any one of [1] to [6], wherein the promoter sequence is selected from the group consisting of a synapsin I promoter sequence, a myelin basic protein promoter sequence, a neuron-specific enolase promoter sequence, a calcium/calmodulin-dependent protein kinase II (CMKII) promoter sequence, a tubulin αI promoter sequence, a platelet-derived growth factor β chain promoter sequence, a glial fibrillary acidic protein (GFAP) promoter sequence, a L7 promoter (cerebellar Purkinje cell specific promoter) sequence and a glutamate receptor delta 2 promoter (cerebellar Purkinje cell specific promoter) sequence.

[9] The virus virion according to [7], wherein the promoter sequence comprises the polynucleotide as set forth in SEQ ID NO: 23 or SEQ ID NO: 24.

[10] The virus virion according to [7], wherein the nucleotide sequence operably linked to the promoter sequence encodes a protein selected from the group consisting of an antibody, a nerve growth factor (NGF), a growth factor (HGF), an acidic fibroblast growth factor (aFGF), a basic fibroblast growth factor (bFGF), a glial cell line-derived neurotrophic factor (GDNF), an aromatic amino acid decarboxylase (AADC) and an amyloid β degrading protease (Neprilysin).

[10a] The virus virion according to [7], wherein the nucleotide sequence operably linked to the promoter sequence expresses dsRNA, siRNA, shRNA or miRNA against the aromatic amino acid decarboxylase (AADC) or α-synuclein.

[11] The virus virion according to [9], wherein the antibody is an antibody against aggregated amyloid β protein.

[11a] The virus virion according to [9], wherein the antibody is a single chain antibody against aggregated amyloid β protein.

[11b] The virus virion according to claim 10, wherein the nucleotide sequence is amyloid β degrading protease (Neprilysin).

[12] The virus virion according to any one of [1] to [11], which is capable of passing through the blood-brain barrier of a subject.

[12a] The virus virion according to any one of [1] to [12] for gene transfer to a nerve cell by peripheral administration to a subject.

[12b] The virus virion according to any one of [1] to [12], wherein the subject is a fetus in the maternal body and the gene is transferred to a nerve cell of the fetus by peripheral administration to the maternal body.

[13] The virus virion according to any one of [1] to [12], wherein the virus virion is an adeno-associated virus vector.

[14] A pharmaceutical composition comprising the virus virion according to any one of [1] to [13].

[15] The pharmaceutical composition according to [14], which reduces aggregated amyloid β protein in the brain of a subject.

[15a] The pharmaceutical composition according to [13], which reduces the level of α-synuclein in nerve cells in the brain of a subject.

[16] The pharmaceutical composition according to [14] or [15], which is a therapeutic agent for Alzheimer's disease.

[16a] The pharmaceutical composition according to [14] or [15a], which is useful for the treatment of Parkinson's disease.

[17] A method comprising a step of administering the virus virion according to any one of [1] to [12] peripherally to a subject.

[17a] The method according to [17], wherein the subject is a fetus in the maternal body and the virus virion is peripherally administered to the maternal body.

[18] The method according to [17], which further comprises a step of reducing aggregated amyloid β protein in the brain of a subject.

[18a] The method according to [17a], which further comprises a step of reducing the level of α-synuclein in nerve cells in the brain of a subject.

[19] The method according to [18] for the treatment of Alzheimer's disease.

[19a] The method according to [18a], which is useful for the treatment of Parkinson's disease.

Effects of the Invention

The recombinant viral vector of the present invention is capable of passing through blood-brain barrier and thus capable of transferring a gene to a nervous system cell in the brain via peripheral administration. In addition, the vector of the present invention can select a therapeutic gene of interest from a broader range, especially in length, by using a non-sc type genome. Therefore, by using the rAAV vector of the present invention that packages the viral genome for carrying the gene of interest encoding a useful protein (which may be one or more), e.g., an antibody, neurotrophic factor, etc., the gene can be transferred to a nervous system cell in the brain, etc. of a subject, through a safe administration method such as peripheral administration, etc. For example, the gene encoding α-synuclein, which is associated with Parkinson's disease, the gene encoding the antibody against amyloid β protein aggregate, which causes Alzheimer's disease, etc. can be incorporated into the recombinant vector of the present invention to provide safer therapeutic drugs for these diseases. Furthermore, the method for producing the virus vector of the present invention and/or the kit of the present invention can be used to prepare the rAAV vector for delivering and transducing a gene of interest to a nervous system cell in a brain or the central nervous system, through peripheral administration with high efficiency.

BRIEF DESCRIPTION OF DRAWINGS

FIG. 1 shows GFP-positive cells in the brain per mouse, using the rAAV virion of the invention.

FIG. 2A shows a picture of the coronal section slice from murine brain tissue after peripheral administration of the yfAAV9-CAG-GFP-containing rAAV vector, and a partially enlarged view. GFP-positive cells are mostly glial cells (arrowhead) (green: GFP, red: NeuN).

FIG. 2B shows a picture of the coronal section slice from murine brain tissue after peripheral administration of the yfAAV9-SynI-GFP-containing rAAV vector, and a partially enlarged view.

FIG. 2C shows a picture of the coronal section slice from murine brain tissue after peripheral administration of the yfAAV9-MBP-GFP-containing rAAV vector, and a partially enlarged view.

FIG. 3 shows GFP-positive cells per 0.04 mm$^3$ of the cerebral cortex, using the rAAV virion of the present invention.

FIG. 4 shows image pictures where nerve cells in which GFP and ChAT in the spinal cord are positive, using the rAAV virion of the present invention, and a partially enlarged view.

FIG. 5 shows an image picture where the results obtained by gene transfer to fetal brain nerve cells through intracardial administration to mother mice using the rAAV virion of the present invention (left), and a partially enlarged view (right).

FIG. 6 shows image pictures where the results of immunostaining of various antibodies in the substantia nigra pars compacta in nerve cells of the mouse brain, by intracardial administration of the yfAAV9-SynI-GFP-miAADC described in Example 3. The primary antibodies used are anti-GFP (left), anti-AADC (center) and anti-TH (right).

MODE FOR CARRYING OUT THE INVENTION

1. Recombinant Adeno-Associated Virus (rAAV) Virion of the Present Invention

In an embodiment, the present invention provides the following rAAV virion defined below:
a recombinant adeno-associated virus virion comprising:
(a) a capsomere which comprises a protein comprising an amino acid sequence having at least 90% identity to the amino acid sequence of SEQ ID NO: 2, 4 or 6, wherein at least one of the surface-exposed tyrosine residues in the amino acid sequence is substituted with another amino acid residue, and the protein is capable of forming a virus virion, and
(b) a polynucleotide packaged in said capsomere which comprises a nervous system cell-specific promoter sequence and a nucleotide sequence operably linked to the promoter sequence.

1.1 Adeno-Associated Virus (AAV)

Naturally occurring adeno-associated virus (AAV) is a non-pathogenic virus. By using this characteristic property, various recombinant viral vectors are constructed and used to deliver a desired gene to achieve gene therapy (see, e.g., WO2003/018821, WO2003/053476, WO2007/001010, Yakugaku Zasshi 126(11) 1021-1028, etc.). A wild type AAV genome is a single-stranded DNA molecule having a full length of approximately 5 kb nucleotides, and is a sense strain or an antisense strain. In general, the AAV genome contains an inverted terminal repeat (ITR) sequence of about a 145 nucleotide length at both 5' and 3' ends of the genome. This ITR is known to have various functions including the function as a replication origin of the AAV genome, the function as a packaging signal of this genome into virions, and so on (see, e.g., Yakugaku Zasshi, 126 (11) 1021-1028 supra, etc.). The internal region of the wild type AAV genome flanked by the ITRs (hereinafter the internal region) contains an AAV replication (rep) gene and a capsid (cap) gene. The rep gene and the cap gene encode, respectively, a protein Rep involved in virus replication and a capsid protein capable of forming a capsomere (e.g., at least one of VP1, VP2 and VP3) which is an outer shell of the regular icosahedral structure. For further details, reference is made to, e.g., Human Gene Therapy, 13, pp. 345-354, 2002, Neuronal Development 45, pp. 92-103, 2001, Jikken Igaku, 20, pp. 1296-1300, 2002, Yakugaku Zasshi, 126(11), 1021-1028, Hum. Gene Ther., 16, 541-550, 2005, etc.

Naturally occurring adeno-associated viruses are known to have various serotypes and to exhibit a preferential tropism for target cells to be infected (which is described in, e.g., Gao, G. et al., Curr. Gene Ther. 5:285-297, 2005, Xin, K-Q, et al., J. Virol. 80: 11899-910, 2006, Hellstroem, M., et al., Gene Ther. 16:521-32, 2009, etc.). Preferably, the rAAV vector of the present invention can be prepared from, but not limited to, naturally occurring adeno-associated virus serotype 1 (AAV1), serotype 2 (AAV2), serotype 3 (AAV3), serotype 4 (AAV4), serotype 5 (AAV5), serotype 6 (AAV6), serotype 7 (AAV7), serotype 8 (AAV8), serotype 9 (AAV9), etc. The nucleotide sequences of these adeno-associated virus genomes are known and referred to as the GenBank accession numbers of AF063497.1 (AAV1), AF043303 (AAV2), NC_001729(AAV3), NC_001829.1 (AAV4), NC_006152.1 (AAV5), AF028704.1 (AAV6), NC_006260.1 (AAV7), NC_006261.1 (AAV8) and AY530579 (AAV9), respectively. Among them, the serotypes 2, 3, 5 and 9 are human-derived. According to the present invention, it is particularly preferred to use the nucleotide sequence encoding the capsid protein derived from AAV1, AAV2 or AAV9. AAV1 and AAV9 were reported to have comparatively high infection efficiency on nerve cells (Taymans, et al., Hum Gene Ther 18:195-206, 2007, etc.). AAV2 has already been clinically applied to gene therapy for Parkinson's disease, etc. (Kaplitt, et al., Lancet 369: 2097-2105, 2007, Marks, et al., Lancet Neurol. 7:400-408, 2008, Christine et al., Neurology 73:1662-1669, 2009, Muramatsu, et al., Mol. Ther. 18:1731-1735, 2010, etc.).

1.2. Capsid Proteins in the rAAV Virion of the Present Invention

In the capsid proteins contained in the rAAV virion of the present invention, at least one of the surface-exposed tyrosine residues (e.g., tyrosine residues with an amino acid side chain exposed on the surface of the virus virion) in the VP1 amino acid sequence (SEQ ID NO: 2, 4 or 6) is substituted with another amino acid. Such proteins include those comprising an amino acid sequence having a sequence identity of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%, to the amino acid sequence of SEQ ID NO: 2, 4 or 6, wherein at least one of the surface-exposed tyrosine residues is substituted with another amino acid, and wherein the protein is capable of forming the virus virion. In general, the larger value for the above number is the more preferable. The capsid protein contained in the rAAV virion of the present invention forms capsomeres alone or in combination with the other capsid protein members (e.g., VP2 and/or VP3, etc.). The rAAV virion of the present invention with the AAV genome (or AAV vector genome) packaged in the capsomere can thus be produced. The rAAV of the present invention is capable of passing through the blood-brain barrier in a living subject (including the blood-brain barrier in an immature fetus and neonate and the blood-brain barrier in an established adult). Moreover, the rAAV virion of the present invention can target nerve cells contained in brains, spinal cords, etc. of adults by peripheral administration. As used herein, the term peripheral administration is used to mean administration routes usually understood by those skilled in the art to be peripheral administration, including intravenous administration, intraarterial administration, intrapericardial administration, intramuscular administration, and umbilical intravascular administration (e.g., the target is a fetus), and so on. The amino acid residues which may be replaced with each other include the other residues among the group of the similar amino acid residues (described below), in which the amino acid residues fall. The capsid proteins modified with the interchangeable amino acid residues can be produced by methods known to those skilled in the art, including conventional genetic engineering techniques, etc. For such genetic engineering procedures, reference may be made to, e.g., Molecular Cloning 3rd Edition, J. Sambrook et al., Cold Spring Harbor Lab. Press. 2001, Current Protocols in Molecular Biology, John Wiley & Sons 1987-1997, etc.

In the capsid proteins contained in the rAAV virion of the present invention, at least one of the surface-exposed tyrosine residues, preferably, at positions 252, 273, 445, 701, 705 and 731 in SEQ ID NO: 2 is substituted with another amino acid, preferably with a phenylalanine residue. Preferably, the tyrosine residue at position 445 is substituted with a phenylalanine residue in the amino acid sequence of SEQ ID NO: 2. In the capsid proteins contained in the rAAV virion of the present invention, at least one of the surface-exposed tyrosine residues, preferably, at positions 252, 272, 444, 500, 700, 704 and 730 in SEQ ID NO: 4 is substituted with another amino acid, preferably with a phenylalanine residue. It is preferred that the tyrosine residue at position 444 is substituted with a phenylalanine residue in the amino acid sequence of SEQ ID NO: 4. In the capsid proteins contained in the rAAV virion of the present invention, one or more of at least one of the surface-exposed tyrosine residues, preferably, at positions 252, 274, 446, 701, 705, 706 and 731 in SEQ ID NO: 8 is substituted with another amino acid, preferably with a phenylalanine residue. It is preferred that the tyrosine residue at position 446 is substituted with a phenylalanine residue in the amino acid sequence of SEQ ID NO: 6. The capsomere in the rAAV virion of the present invention may either contain the above protein alone or in further combination with other members (VP2 and/or VP3). According to the present invention, the substitution at the position of the amino acid residue includes the substitution of the amino acid residue at the corresponding position in the VP2 and VP3 from each of the virus serotypes, and preferably, the substitution of such corresponding tyrosine residue with a phenylalanine residue. These modified capsid proteins may be prepared by methods known to those skilled in the art including conventional genetic engineering techniques, etc. For these genetic engineering procedures, reference is made to, e.g., Molecular Cloning, 3rd Edition, etc. The virus virions of the present invention containing these capsid proteins are capable of passing through adult and fetus blood-brain barriers as described above. Preferably, the virus virions containing the functionally equivalent capsid proteins can infect nervous system cells in brains, spinal cords, etc. of adults, through peripheral administration. The term nervous system as used herein refers to the organ system made up of nerve tissues. In the present invention, nervous system cells as a target for gene transfer include at least neurons located in the central nervous system including brains, spinal cords, etc. and may further include glial cells, microglial cells, astrocytes, oligodendrocytes, ependymocytes, cerebrovascular endothelial cells, etc. The ratio of the gene-transferred nerve cells of the gene-transferred nervous system cells is preferably 70% or more, 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more, or 100%.

The rAAV virion of the present invention also comprises the amino acid sequence of SEQ ID NO: 8, 10 or 12, or an amino acid sequence, in which one or more amino acids are deleted, substituted, inserted and/or added at positions other than the positions 444 to 446 in the amino acid sequence of SEQ ID NO: 8, 10 or 12, and comprises a protein still capable of forming virus virions. In more detail, the capsid proteins contained in the rAAV virion of the present invention are contained in the capsomere of the rAAV virion of the present invention, alone or in combination with the other capsid protein members (e.g., VP2 and/or VP3, etc.), and the AAV genome (or the recombinant AAV vector genome) is packaged inside the capsomere. In the deletion, substitution, insertion and addition of amino acids described above, two or more modifications may be made at the same time. Examples of these proteins include the proteins having the amino acid sequence of SEQ ID NO: 8, 10 or 12, or those containing an amino acid sequence, in which, e.g., 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue is deleted, substituted, inserted and/or added at positions other than the positions 444 to 446 in the amino acid sequence of SEQ ID NO: 8, 10 or 12, and wherein the protein is capable of forming a virus virion. In general, the smaller the number of the above-described amino acid residues to be deleted, substituted, inserted and/or added is, the more preferred. The rAAV virion produced in the present invention can pass through adult and fetus blood-brain barriers as described above, which enables gene transfer to nerve cells in the brain, spinal cord, etc., preferably through peripheral administration. Furthermore, the rAAV virion of the present invention can transfer a gene to a nervous system cell contained in a fetal brain, spinal cord or the like in a maternal body by peripheral administration to the maternal body. These modified capsid proteins can be prepared in accordance with methods known to those skilled in the art, including conventional genetic engineering techniques, etc.

Examples of the amino acid residues which are interchangeable in the protein (polypeptide) of the present invention are given below. The amino acid residues in the same group are interchangeable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The aforesaid capsid proteins VP1, VP2 and/or VP3 contained in the rAAV virion of the present invention can be encoded by one or more polynucleotides. Preferably, the capsid proteins in the present invention are all encoded by one polynucleotide. More preferably, the capsid proteins are encoded by the polynucleotide of SEQ ID NO: 7, 9 or 11.

The polynucleotides which encodes the capsid proteins contained in the rAAV virion of the present invention encode proteins that are functionally equivalent to the capsid proteins capable of forming the recombinant virus virion of the present invention. Such polynucleotides include, for example, a polynucleotide sequence of SEQ ID NO: 7, 9 or 11, or a polynucleotide sequence containing SEQ ID NO: 7, 9 or 11, in which, e.g., at least one (e.g., 1 to 50, 1 to 40, 1 to 30, 1 to 25, 1 to 20, 1 to 15, 1 to 10, 1 to 9 (1 to several), 1 to 8, 1 to 7, 1 to 6, 1 to 5, 1 to 4, 1 to 3, 1 to 2 and 1) nucleotide is deleted, substituted, inserted and/or added, and said polynucleotide encoding a protein comprising the amino acid sequence of SEQ ID NO: 8, 10 or 12, and a protein comprising an amino acid sequence in which 1 or more amino acids are deleted, substituted, inserted and/or added at positions other than positions 444 to 446 in the amino acid sequence of SEQ ID NO: 8, 10 or 12, and wherein the protein is capable of forming a virus virion. In these deletion, substitution, insertion and/or addition, two or more modifications may be made at the same time. The rAAV virion of the present invention comprising the capsid protein encoded by the polynucleotide is capable of passing through the blood-brain barriers of the adult and fetus, as described above. Preferably, the rAAV virion of the present invention can transfer a gene to nervous system cells contained in the adult brain, spinal cord, etc. through peripheral administration. The rAAV virion of the present invention can also transfer genes to nervous system cells contained in the fetal brain, spinal cord, etc. in the maternal body through peripheral administration to the maternal body. In general, the smaller number of the nucleotides that are deleted, substituted, inserted and/or added as described above is, the more preferred. Such a polynucleotide may include, for example, a polynucleotide which is hybridizable under stringent hybridization conditions to SEQ ID NO: 7, 9 or 11 or its complementary sequence and encodes a protein capable of forming the recombinant virus virion of the present invention (e.g., a protein comprising the amino acid sequence of SEQ ID NO: 8, 10 or 11, or an amino acid sequence in which 1 or more amino acids are deleted, substituted, inserted and/or added at positions other than the positions 444 to 446 in the amino acid sequence of SEQ ID NO: 8, 10 or 12).

The hybridization may be performed by well-known methods or methods modified therefrom, for example, methods described in Molecular Cloning (3rd Edition, J. Sambrook et al., Cold Spring Harbor Lab. Press. 2001), etc. When commercially-available libraries are used, the hybridization may be performed by the methods described in instructions provided by manufacturers, etc. As used herein, the term "stringent conditions" may be any of low stringent conditions, moderate stringent conditions and high stringent conditions. The term "low stringent conditions" refers to conditions of, for example, 5×SSC, 5×Denhardt's solution, 0.5% SDS, 50% formamide at 32° C. The term "moderate stringent conditions" refers to conditions of, for example, 5×SSC, 5×Denhardt's solution, 0.5% SDS, 50% formamide at 42° C. The term "high stringent conditions" refers to conditions of, for example, 5×SSC, 5×Denhardt's solution, 0.5% SDS, 50% formamide at 50° C. Under these conditions, a DNA with higher homology is expected to be obtained efficiently at higher temperatures, although multiple factors are involved in hybridization stringency including temperature, probe concentration, probe length, ionic strength, time, salt concentration and others, and one skilled in the art may appropriately select these factors to achieve similar stringency.

The polynucleotide which is hybridizable include polynucleotides having, e.g., 70% or higher, 80% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity, to the nucleotide sequence of SEQ ID NO: 7, 9 or 11, as calculated using homology search software, such as FASTA and BLAST using default parameters. In general, the larger numerical value of the homology above is the more preferred.

The identity between amino acid sequences or polynucleotide sequences may be determined using the algorithm BLAST by Karlin and Altschul (Proc. Natl. Acad. Sci. USA, 87: 2264-2268, 1990; Proc. Nail Acad. Sci. USA, 90: 5873, 1993). Programs called BLASTN and BLASTX based on the BLAST algorithm have been developed (Altschul S. F. et al., J. Mol. Biol. 215: 403, 1990). When a nucleotide sequence is analyzed using BLASTN, the parameters are, for example, score=100 and wordlength=12. When an amino acid sequence is analyzed using BLASTX, the parameters are, for example, score=50 and wordlength=3. When BLAST and Gapped BLAST programs are used, default parameters for each of the programs are employed.

The Rep proteins used in the present invention may have a sequence identity of the same value as the above and may contain deletion, substitution, insertion and/or addition in the same number of the amino acid residues as the above, as far as they have known functions with the functionally equivalent level, including the function of recognizing the ITR sequence to perform genome replication depending on the sequence, the function of recruiting and packaging wild type AAV genome (or rAAV genome) into the virus virion, the function of forming the rAAV virion of the present invention, etc. The functionally equivalent level includes a range as described above for the specific activity. In the present invention, the Rep protein derived from known AAV3 is preferably used. More preferably, the protein having the amino acid sequence set forth in SEQ ID NO: 16 is used.

The polynucleotide encoding the Rep proteins used in the present invention may have a sequence identity of the same value as the above and may contain deletion, substitution, insertion and/or addition of the same number of the amino acid residues as the above, as far as it has known functions with the functionally equivalent level, including the function of recognizing the ITR sequence to perform genome replication depending on the sequence, the function of recruiting and packaging wild type AAV genome (or rAAV genome) into the virus virion, the function of forming the rAAV virion of the present invention, etc. The functionally equivalent level includes a range as described above for the specific activity. In the present invention, the rep gene derived from AAV3 is preferably used. More preferably, the polynucleotide having the nucleotide sequence set forth in SEQ ID NO: 15 is used.

In one embodiment of the present invention, the capsid proteins VP1 and the like (VP1, VP2 and/or VP3) encoded by the internal region of wild type AAV genome described above and the Rep proteins are provided in such a form that the polynucleotide encoding them is incorporated into the AAV helper plasmid of the present invention. The capsid proteins (VP1, VP2 and/or VP3) and Rep proteins used in the present invention may be incorporated into 1, 2, 3 or more plasmids, if necessary. Optionally, at least one of these capsid proteins and Rep proteins may be incorporated into the AAV genome. In the present invention, it is preferred that the capsid proteins VP1 and the like (VP1, VP2 and/or VP3) and Rep proteins are all encoded by one polynucleotide and provided as the AAV helper plasmid. Reference may be made to, e.g., EXAMPLES hereinafter.

1.3. rAAV Genome of the Present Invention

The recombinant adeno-associated virus genome packaged into the rAAV virion of the present invention (hereinafter the rAAV genome of the present invention) can be produced by replacing the polynucleotide in the internal region between the ITRs located at the 5' and 3' sides of a wild type genome (namely, one or both of the rep gene and cap gene), with a gene cassette comprising a polynucleotide (therapeutic gene) encoding the protein of interest and a promoter sequence for transcribing the polynucleotide, etc. It is preferred that the ITRs at the 5' and 3' sides are located at the 5' and 3' ends of the AAV genome, respectively. Preferably, in the rAAV genome of the present invention, the ITRs located at the 5' and 3' ends include the ITR at the 5' side and the ITR at the 3' side contained in the AAV1, AAV2, AAV3 or AAV9 genome. Particularly preferably, the virus genome packaged into the rAAV virion of the present invention is the polynucleotide of SEQ ID NO: 13 for the ITR at the 5' side and the polynucleotide of SEQ ID NO: 14 for the ITR at the 3' side. In general, the ITR portion takes the sequence wherein the complementary sequence is easily replaced (flip and flop structure), and the 5' to 3' direction may be reversed in the ITR contained in the rAAV genome of the present invention. In the rAAV genome of the present invention, the length of the polynucleotide (i.e., therapeutic gene) which is replaced for the internal region is preferably similar to the length of parent polynucleotide from a practical viewpoint. Specifically, it is preferred that the rAAV genome of the present invention has almost the same size in full length as 5 kb, which is a full length of the wild type, for example, about 2 to 6 kb, preferably about 4 to 6 kb.

When the length of transcription regulatory region including a promoter, polyadenylation, etc. is deduced (assuming that the length is e.g., about 1 to 1.5 kb), the size of a therapeutic gene incorporated into the rAAV genome of the present invention is preferably about 0.01 to 3.7 kb, more preferably, about 0.01 to 2.5 kb, and most preferably, about 0.01 to 2 kb, in length, but not limited thereto. Two or more therapeutic genes of about 0.01 to 1.5 kb may also be co-incorporated by known techniques using, e.g., a known internal ribosome entry site (IRES) sequence, as far as the full length of the rAAV genome is within the range described above.

In general, the viral genome packaged in a recombinant adeno-associated virus virion involves a problem that it takes time (several days) until the gene of interest in the genome is expressed, because the genome is single-stranded. To solve the problem, it is attempted to design a therapeutic gene introduced to be self-complementary (called a self-complementary (sc) vector), thereby to promote the expression after infection with the virus vector. In this case, the length of a therapeutic gene described above should be designed to be almost half the length of non-sc genome vector, since it is necessary to contain an inverted sequence to produce a double strand. More specifically, in case of converting a recombinant viral genome to the sc type, the length of a gene of interest that can be incorporated is designed to be approximately 2 kb, including the regions required for a promoter, polyadenylation, etc. Details for specific procedures are described in, e.g., Foust K. D., et al. supra (Nat. Biotechnol. 2009 January; 27(1): 59-65, Non-Patent Document 3), etc. In the present invention, when the length of a gene of interest is short, the sc genome vector may also be used. That is, the rAAV genome used in the present invention may be a non-sc type or a sc type. In the case of the sc type, the whole expression cassette containing a gene of interest or a part thereof can form a double-stranded DNA.

In order to express a polypeptide of interest in the rAAV genome of the present invention, a polynucleotide sequence encoding the polypeptide is operably combined with various known promoter sequences. However, when using a rAAV vector carrying, for example, a CMV promoter, which is a usually available and strong promoter, most of the genes of interest were introduced in glia-like cells, not in nerve cells, in the adult subject (cf., e.g., Example 1 herein below). Therefore, the promoter sequence used in the rAAV virion of the present invention is to be specific to nervous system cells. As defined above, the term nervous system as used herein refers to the organ system made up of nerve tissues. In the present invention, the nervous system cell-specific promoter sequences used in the present invention are derived from, e.g., nerve cells, glial cells, oligodendrocytes, cerebrovascular endothelial cells, microglial cells, ependymocytes, etc., but not limited thereto. Specific examples of such promoter sequences include, but are not limited to, a synapsin I promoter sequence, a myelin basic protein promoter sequence, a neuron-specific enolase promoter sequence, a glial fibrillary acidic protein promoter sequence, a L7 promoter sequence (cerebellar Purkinje cell specific promoter) and a glutamate receptor delta 2 promoter (cerebellar Purkinje cell specific promoter). In the rAAV virion of the present invention, promoter sequences such as a calcium/calmodulin-dependent protein kinase II (CMKII) promoter, a tubulin αI promoter, a platelet-derived growth factor β chain promoter, etc. may also be used. These promoter sequences may be used alone or in optional combination of two or more thereof. Particularly preferred are the synapsin I promoter sequence and the myelin basic protein promoter sequence. The rAAV genome of the present invention may further contain known sequences such as an enhancer sequence which assists in transcription of mRNA, translation into a protein, etc., a Kozak sequence, an appropriate polyadenylation signal sequence, etc.

A therapeutic gene of interest is incorporated into the rAAV genome of the present invention. The therapeutic gene may encode a protein used to treat various diseases. The protein encoded may be one or more, while the rAAV genome to be packaged should be approximately 5 kb or less in length (approximately 4.7 kb or less except for the ITR region), including the gene of interest. When the rAAV genome to be packaged is, for example, the non-sc type, the length of the gene of interest incorporated in the rAAV genome is substantially limited to approximately 3.5 kb or less; when the genome is in the sc type, the length is further limited to a half length of the above. Accordingly, in a further embodiment, a polynucleotide encoding a protein consisting of a short polypeptide is preferably used for a therapeutic gene of interest. Examples of such proteins include, but not limited to, an antibody (including an antigen-binding site, Fab, Fab2, a single chain antibody (scFv), etc.), nerve growth factor (NGF), growth factor (HGF), acidic fibroblast growth factor (aFGF), brain-derived neurotrophic factor (BDNF), neurotrophins NT-3 and NT-4/5, ciliary neurotrophic factor (CNTF), glial cell line-derived neurotrophic factor (GDNF), neurturin, any one of the heregluin/neuregulin/ARIA/neu differentiation factor (NDF) family of agrin, semaphorins/collapsins, netrin-1 and netrin-2, basic fibroblast growth factor (bFGF), glial cell line derived neurotrophic factor (GDNF), aromatic amino acid decarboxylase (AADC), amyloid β degrading protease (Neprilysin), etc. Genes associated with metabolic enzyme diseases that cause neurological disorders (e.g., mucopolysaccharidosis including Gaucher's disease, amino acid metabolism abnormality including homocystinuria, lipid metabolism abnormalities including metachromatic leukodystrophy, etc.) may be incorporated as well and examples of the genes include the genes encoding glucocerebrosidase, cystathionine, β-synthase, arylsulfatase A, etc.

In a still further embodiment of the present invention, the class of antibody encoded by the rAAV genome of the present invention includes, but not particularly limited to, an antibody of any isotype of IgG, IgM, IgA, IgD, IgE, etc. However, it should be noted that the length of the polynucleotide encoding the antibody is practically limited. As used herein, the term "antibody" means to include any antibody fragment or derivative thereof, and includes, for example, Fab, Fab'2, CDR, a humanized antibody, a chimeric antibody, a multifunctional antibody, a single chain antibody (ScFv), etc. In the present invention, the polynucleotide encoding a single chain antibody (ScFv) is preferably used as the therapeutic gene of interest.

The protein encoded by the rAAV genome of the present invention may contain protein variants with insertion, deletion, substitution and/or addition of amino acid residues by genetic engineering, as far as the protein performs the intended functions. In the insertion, deletion, substitution and/or addition, two or more modifications may be made on these protein variants at the same time. Preferably, these protein variants have functions equivalent to those of their parent proteins (e.g., the antigen-binding ability). These protein variants preferably include proteins consisting of, e.g., the amino acid sequence of anti-amyloid β protein (Aβ) single chain antibody (scFv), in which, e.g., 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue is deleted, substituted, inserted and/or added, while the protein has the antigen-binding ability equivalent to that of the parent proteins. In the present invention, the term "having equivalent functions" is intended to mean to have the antibody-binding ability that the specific activity is in the range of, e.g., 0.01 to 100-fold, preferably approximately 0.5 to 20-fold, and more preferably, approximately 0.5 to 2-fold, but is not limited thereto.

The therapeutic gene of interest which is incorporated into the rAAV genome of the present invention may be a polynucleotide that alters (e.g., destroys or diminishes) the functions of targeted endogenous genes, including an antisense molecule, ribozyme, interfering RNA (iRNA) or microRNA (miRNA), or a polynucleotide that alters (e.g., down-regulates) the expression levels of the endogenous proteins. The genes to be targeted are those responsible for various diseases and include, but not limited to, a gene encoding α-synuclein associated with Parkinson's diseases, various known oncogenes that cause cancers. To effectively suppress the expression of a gene of interest using, e.g., an antisense sequence, the length of the antisense nucleic acid is preferably at least 10 nucleotides, 15 nucleotides or more, 20 nucleotides or more, 100 nucleotides or more, and more preferably, 500 nucleotides or more. Usually, the length of an antisense nucleic acid to be used is shorter than 5 kb, and preferably, shorter than 2.5 kb.

By using a ribozyme, the mRNA for the target protein can be specifically cleaved to down-regulate the expression of the protein. For the design of such a ribozyme, reference may be made to various known publications (cf., e.g., FEBS Lett. 228: 228, 1988; FEBS Lett. 239: 285, 1988; Nucl. Acids. Res. 17: 7059, 1989; Nature 323: 349, 1986; Nucl. Acids. Res. 19: 6751, 1991; Protein Eng 3: 733, 1990; Nucl. Acids Res. 19: 3875, 1991; Nucl. Acids Res. 19: 5125, 1991; Biochem. Biophys. Res. Commun. 186: 1271, 1992, etc.).

The term "RNAi" is intended to refer to a phenomenon that when a double stranded RNA with a sequence identical or similar to the target gene sequence is introduced into cells, expression of both the foreign gene introduced and the endogenous target gene is down-regulated. The RNA used herein includes, for example, double-stranded RNA of 21 to 25 nucleotides in length that triggers RNA interference, such as dsRNA (double strand RNA), siRNA (small interfering RNA), shRNA (short hairpin RNA) or miRNA (microRNA). These RNAs may be locally delivered to a desired site by a delivery system using liposomes, or a vector that generates the double-stranded RNA described above may be used for local expression thereof. Methods for producing or using such double-stranded RNA (dsRNA, siRNA or shRNA) are known from many publications (see, e.g., Japanese National Publication (Tokuhyo) 2002-516062, US 2002/086356A, Nature Genetics, 24(2), 180-183, 2000 February; Genesis, 26 (4), 240-244, 2000 April; Nature, 407:6802, 319-20, 2002 Sep. 21; Genes & Dev., Vol. 16 (8), 948-958, 2002 Apr. 15; Proc. Natl. Acad. Sci. USA, 99(8), 5515-5520, 2002 Apr. 16; Science, 296(5567), 550-553, 2002 Apr. 19; Proc Natl. Acad. Sci. USA, 99: 9, 6047-6052, 2002 Apr. 30; Nature Biotechnology, Vol. 20 (5), 497-500, 2002 May; Nature Biotechnology, Vol. 20 (5), 500-505, 2002 May; Nucleic Acids Res., 30:10, e46, 2002 May 15, etc.).

As used herein, the terms "virus virion," "virus or viral vector" and "viral particle" are interchangeably used, unless otherwise indicated.

As used herein, the term "polynucleotide" is interchangeably used with "nucleic acid," "gene" or "nucleic acid molecule," which is intended to mean a nucleotide polymer. As used herein, the term "nucleotide sequence" is used exchangeably with "nucleic acid sequence" or "nucleotide sequence," which is represented by a sequence of deoxyribonucleotides (abbreviated as A, G, C, and T). For example, the "polynucleotide comprising the nucleotide sequence of SEQ ID NO: 1 or a fragment thereof" is intended to mean a polynucleotide comprising a sequence shown by the respective deoxynucleotides A, G, C and/r T of SEQ ID NO: 1, or a fragment thereof.

Each of "viral genome" and "polynucleotide" used in the present invention may exist in the form of a DNA (e.g., cDNA or genomic DNA), respectively, and may also be in the form of an RNA (e.g., mRNA). Each of the viral genome and the polynucleotide as used herein may be a double stranded or single stranded DNA. Single-stranded DNA or RNA may be a coding strand (also known as a sense strand) or a non-coding strand (also known as an anti-sense strand). Regarding the explanation herein for placing a promoter, a gene of interest, polyadenylation signal, etc. in the gene that are encoded by the rAAV genome, if the rAAV genome is a sense strand, the strand itself is described and if it is an antisense strand, its complementary strand is described, unless otherwise specified.

As used herein, the terms "protein" and "polypeptide" are interchangeably used and intended to mean a polymer of amino acids. The polypeptide as used herein is represented in accordance with conventional peptide designation, in which the N-terminus (amino terminus) is at the left hand and the C-terminus (carboxyl terminus) at the right hand. The partial peptide in the polypeptide of the present invention (in case, briefly referred to as the partial peptide of the present invention) includes a partial peptide of the polypeptide of the present invention described above, and preferably having the same properties as those of the polypeptide of the present invention.

As used herein, the term "plasmid" means various known gene elements, for example, a plasmid, phage, transposon, cosmid, chromosome, etc. The plasmid can be replicated in a particular host and transfer gene sequences between cells. As used herein, the plasmid contains various known nucleotides (DNA, RNA, PNA and a mixture thereof) and may be a single strand or a double strand, and preferably a double strand. As used herein, the term "rAAV vector plasmid" is intended to include a double strand formed by rAAV vector genome and its complementary strand, unless otherwise stated. The plasmid used in the present invention may be linear or circular.

The therapeutic gene of interest which is incorporated in the rAAV genome of the present invention is transferred to a nervous system cell with a higher efficiency than before and then incorporated into the genome of the cell. The gene can be transferred to a larger number of nerve cells, which count is approximately 10 times or more, approximately 20 times or more, approximately 30 times or more, approximately 40 times or more, or approximately 50 times or more, when using the rAAV vector of the present invention, as compared to using a conventional rAAV vector. The number of nerve cells carrying the gene transferred thereto can be determined, e.g., by producing an rAAV virion which has a packaged rAAV vector genome with any marker gene incorporated therein, administering the rAAV virion to an animal, and then measuring the number of nervous system cells which express the marker gene (or marker protein) incorporated in the rAAV vector genome. The marker gene to be used is selected from known genes. Examples of such marker genes include LacZ gene, green fluorescence protein (GFP) gene, light emitting protein gene (firefly luciferase, etc.), etc.

In the present invention, an rAAV virion which has an rAAV vector genome packaged can pass through the blood-brain barrier in a living subject. Thus, the therapeutic gene of interest can be transferred to nervous system cells in the brain, spinal cord, etc. of the subject, through peripheral administration to the subject. In case that the rAAV genome of the present invention is a non-sc type, the promoter and the gene of interest may be chosen from a broader range of length. A plurality of the genes of interest may be used as well.

As use herein, the term "packaging" refers to the events including production of single-strand viral genomes, assembly of coat (capsid) proteins, encapsidation of viral genomes, and the like. When an appropriate plasmid vector (normally, a plurality of plasmids) is introduced into a cell line that allows packaging under an appropriate condition, recombinant viral particles (i.e., virus virions, viral vectors) are constructed and secreted into the culture.

2. Production of the rAAV Virion of the Present Invention

In a still further embodiment of the present invention, the invention provides a method for producing the rAAV virion of the present invention. The method may comprise the step of transfecting a cultured cell with: (a) a first polynucleotide which encodes the capsid protein of the present invention (generally called an AAV helper plasmid), and (b) a second polynucleotide (carrying a therapeutic gene of interest) to be packaged in the rAAV virion of the present invention; and may further include the step of transfecting the cultured cell with (c) a plasmid encoding an adenovirus-derived factor, also referred to as an adenovirus (AdV) helper plasmid, or the step of infecting the cultured cell with an adenovirus. The method may also include the step of culturing the transfected cultured cell and collecting the recombinant adeno-associated virus vector from culture supernatant. This method is already known and also used in EXAMPLES below.

Preferably, the method for producing the rAAV virion of the present invention comprises transfecting a cultured cell with: (a) a first polynucleotide encoding a protein comprising an amino acid sequence selected from the group consisting of SEQ ID NOs: 8, 10 and 12, and (b) a second polynucleotide comprising a polynucleotide carrying a nervous system cell-specific promoter sequence and a polynucleotide operably linked to the promoter sequence between the nucleotide sequence of SEQ ID NO: 13 and the nucleotide sequence of SEQ ID NO: 14. The first and the second polynucleotides include, for example, the combinations of the polynucleotides as listed in TABLE 1 of EXAMPLES.

Preferably, the nucleotide encoding the capsid protein of the present invention in the first polynucleotide is operably linked to a known promoter sequence that can work in a cultured cell. Examples of such a promoter sequence include cytomegalovirus (CMV) promoter, EF-1α promoter, SV40 promoter, etc., which may be suitably used. The polynucleotide may further contain a known enhancer sequence, Kozak sequence, poly(A) addition signal sequence, etc. appropriately.

The second polynucleotide contains a therapeutic gene at a location operable with the nervous system cell-specific promoter. The polynucleotide may appropriately contain a known enhancer sequence, Kozak sequence, poly(A) addition signal sequence, etc. The first polynucleotide may further contain a cloning site that can be cleaved by various known restriction enzymes downstream from the nervous system cell-specific promoter sequence. A multicloning site containing a plurality of restriction enzyme sites is more preferred. A person skilled in the art may incorporate a therapeutic gene of interest at the downstream of the nervous system cell-specific promoter sequence, in accordance with known genetic engineering procedures. For such genetic engineering procedures, see, e.g., Molecular Cloning 3rd Edition, J. Sambrook et al., Cold Spring Harbor Lab. Press. 2001, etc.

Since an AAV is a helper-dependent virus, it is necessary to co-infect a virion-producing cell (cultured cell) with a helper virus (e.g., adenovirus, herpes virus or vaccinia) upon infection in order to produce the rAAV virion of the present invention. Without co-infection with a helper virus, the viral genome is inserted into a host cell chromosome but any infectious AAV virion derived from the viral genome inserted is not produced. When the host with the inserted viral genome is infected with a helper virus, the infectious AAV virion from the inserted genome may be produced. AAV itself may infect cells from different species while it is required that a helper virus be the same species as a host cell. For example, human AAV can be replicated in canine cells co-infected with canine adenovirus.

In producing the rAAV virion of the present invention, the first and the second polynucleotides as described above can be co-introduced into cultured cells, using a helper virus plasmid (e.g., adenovirus, herpesvirus or vaccinia). Preferably, the production method of the present invention further comprises the step of introducing an adenovirus (AdV) helper plasmid. The AdV helper plasmid encodes proteins such as E1a, E1b, E2a, E4 orf4, etc. which are required for AAV genome replication, etc. Alternatively, a recombinant viral or non-viral vector (e.g., plasmid, episome, etc.) that conveys a necessary helper function may also be used. These recombinant viruses may be produced in accordance with techniques already known and published in the art. A variety of adenovirus cell lines is available from ATCC (American Type Culture Collection) and is also commercially available. Alternatively, the sequences of many adenovirus cell lines are available from, e.g., public databases (e.g., PubMed, Genbank, etc.).

In the present invention, it is preferred to derive the AdV helper from a virus for the same species as the cultured cells. For example, when human cultured cells 293T are used, a human AdV-derived helper virus vector may be used. Commercially available vectors (e.g., Agilent Technologies, AAV Helper-Free System (Catalog No. 240071)) may be used as such AdV helper vectors.

In producing the rAAV virion of the present invention, various known methods including, e.g., the calcium phosphate method, lipofection method, electroporation method, etc. may be used in the method for transfecting one or more plasmids as described above to cultured cells. Such methods are described in, e.g., Molecular Cloning 3rd Ed., Current Protocols in Molecular Biology, John Wiley & Sons 1987-1997, etc.

3. Pharmaceutical Composition Comprising the rAAV Virion of the Present Invention In a still further embodiment of the present invention, a pharmaceutical composition comprising the rAAV virion (rAAV vector) of the present invention is provided. Using the pharmaceutical composition comprising the rAAV virion of the present invention (hereinafter referred to as the present pharmaceutical composition), a gene can be introduced into nervous system cells of a subject with a high efficiency, and a method is provided in which a disease of interest can be treated with the introduced gene. The rAAV can pass through the blood-brain barrier in a living subject and hence, the rAAV of the present invention can be delivered to nervous system cells in the brain, spinal cord, etc. of a living subject through peripheral administration to the subject. That is, when the rAAV of the present invention is used, an administration route which requires more careful handling such as intraparenchymal administration is not required so that higher safety can be expected.

In one embodiment, the rAAV virion of the present invention preferably comprises a nervous system cell-specific promoter sequence and a therapeutic gene operably linked to the promoter sequence. The rAAV virion of the present invention may contain a gene which is useful for the treatment of neurological disorders (e.g., Parkinson's disease, Alzheimer's disease, triplet repeat disease, prion disease, amyotrophic lateral sclerosis, spinocerebellar degeneration, channel disease, epilepsy, etc.), inborn errors of metabolism (Wilson's disease, peroxisome disease, etc.), demyelinating disorders (multiple sclerosis, etc.), central neuron infectious diseases (e.g., HIV encephalitis, bacterial meningitis, etc.), vascular disorders (cerebral infarction, cerebral hemorrhage, spinal cord infarction), trauma (cerebral contusion, spinal cord injury, etc.), retinal disorders (age-related macular degeneration, diabetic retinopathy, etc.), and so on. Therefore, the useful treating gene is allowed to pass through the blood-brain barrier and to be incorporated into nerve cells in the brain, spinal cord or retina, e.g. the rAAV virion carrying such a therapeutic gene is included in the pharmaceutical composition of the present invention. These therapeutic genes may be a polynucleotide selected from those encoding the antibody, nerve growth factor (NGF), growth factor (HGF), acidic fibroblast growth factor (aFGF), etc. described above. The therapeutic gene of interest associated with Parkinson's disease includes, for example, an antisense polynucleotide, RNAi, etc. that down-regulate the expression of α-synuclein. The rAAV virion used to treat Alzheimer's disease can be produced by choosing, e.g., the polynucleotide encoding a single chain antibody capable of recognizing aggregated amyloid β protein. It can be expected to treat neurological disorders such as Parkinson's disease, Alzheimer's disease, etc., by peripheral administration of such rAAV virion to a subject. For example, the pharmaceutical composition of the present invention can reduce the expression level of α-synuclein, e.g., in nerve cells in the patient's brain and is useful for the treatment of Parkinson's disease. Furthermore, by expressing an antibody against aggregated amyloid β protein, the pharmaceutical composition can reduce the aggregated amyloid β protein in the patient's brain and is thus useful for the treatment of Alzheimer's disease.

When the pharmaceutical composition of the present invention is used, the composition may be administered, e.g., orally, parenterally (intravenously), intramuscularly, through the oral mucosa, rectally, intravaginally, subcutaneously, intranasally, by inhalation, etc., preferably, parenterally, and more preferably, intravenously. The active ingredient in the pharmaceutical composition of the present invention may be formulated alone or in combination therein, and may also be provided as a pharmaceutical preparation by formulation with a pharmaceutically acceptable carrier or an additive for a pharmaceutical preparation. In this case, the active ingredient of the present invention may be contained by, e.g., 0.1 to 99.9 wt % in the preparation.

Examples of the pharmaceutically acceptable carriers or additives which may be used include excipients, disintegrants, disintegration aids, binders, lubricants, coating agents, dyes, diluents, dissolution agents, dissolution aids, isotonic agents, pH regulators, stabilizers, etc.

Examples of the pharmaceutical preparations suitable for oral administration may include powders, tablets, capsules, fine granules, granules, liquid or syrup, etc. For oral administration, various excipients such as microcrystalline cellulose, sodium citrate, calcium carbonate, dipotassium phosphate and glycine may be employed in combination with various disintegrants such as starch and preferably corn, potato or tapioca starch, alginic acid and certain silicate complexes; and various granulation binders such as polyvinylpyrrolidone, sucrose, gelatin, gum arabic, etc. Additionally, lubricants such as magnesium stearate, sodium lauryl sulfate, talc, etc. are often very useful for tableting purposes. Such solid compositions may also be employed by encapsulation in gelatin capsules. Preferred materials in relation to this further may include lactose or milk sugar, as well as high molecular weight polyethylene glycols. When aqueous suspensions and/or elixirs are desired for oral administration, the active ingredient may be used in combination with various sweeteners or corrigents, coloring agents or dyes, and, if necessary, emulsifying and/or suspending agents as well, together with diluents such as water, ethanol, propylene glycol, glycerin, etc. and combinations thereof.

Examples of the pharmaceutical preparations suitable for parenteral administration include injections, suppositories, etc. For parenteral administration, solutions of the active ingredient of the present invention in either sesame or peanut oil or in aqueous propylene glycol solution may be employed. The aqueous solutions should be appropriately buffered (preferably pH of 8 or higher) depending upon necessity; it is first necessary to render the liquid diluent isotonic. Such a liquid diluent includes, for example, physiological saline. These aqueous solutions prepared are suitable for intravenous injection. On the other hand, the oily solutions are suitable for intra-articular, intra-muscular and subcutaneous injection. The preparation of all these solutions under sterile conditions can be readily accomplished by standard pharmaceutical techniques well known to those skilled in the art. Furthermore, the active ingredient of the present invention may also be administered topically to the skin, etc. In this case, topical administration is preferred by way of creams, jellies, gels, pastes, ointments and the like, in accordance with standard pharmaceutical practice.

The dose of the pharmaceutical composition of the present invention is not particularly limited, and an appropriate dose can be chosen depending on various conditions such as type of disease, age and symptoms of the patient, administration route, therapeutic goal, presence or absence of concurrent drugs, etc. The dose of the pharmaceutical composition of the present invention is, but not limited to, for example, 1 to 5,000 mg, and preferably 10 to 1,000 mg per day for an adult (e.g., body weight of 60 kg). The composition of such daily dosage may be administered daily in 2 to 4 divided doses. When vg (vector genome) is used as a dosage unit, the dose may be chosen from, but not limited to, e.g., the range from $10^9$ to $10^{14}$ vg, preferably, $10^{10}$ to $10^{13}$ vg, and more preferably, $10^{10}$ to $10^{12}$ vg per body weight of 1 kg.

4. Method for Transferring Genes to a Living Subject Using the rAAV Virion of the Present Invention In a still further embodiment, the present invention provides a method for transferring a gene to a nervous system cell in a living subject, which comprises using the rAAV virion of the present invention (hereinafter referred to as the method of the present invention). Specifically, the method of the present invention comprises the step of peripherally administering the rAAV virion of the present invention to a subject. The method of the present invention further comprises the step of delivering a therapeutic gene contained in the rAAV virion of the present invention to a nervous system cell in the brain, spinal cord, etc. The rAAV virion of the present invention is capable of passing through the blood-brain barrier of a living subject (including an adult and a fetus) as described above. Thus, administration routes like intracerebral administration that require more careful handling are not required, and higher safety can be expected.

In a still further embodiment, the rAAV virion of the present invention preferably comprises a recombinant viral genome comprising the nervous system cell-specific promoter sequence and a therapeutic gene operably linked to the promoter sequence (such a viral genome is packaged). As these therapeutic genes, a polynucleotide may be selected from those encoding the antibody, nerve growth factor (NGF), growth factor (HGF), acidic fibroblast growth factor (aFGF), etc., described above. In a still further embodiment of the present invention, the rAAV virion comprising a polynucleotide encoding a single chain antibody capable of recognizing, e.g., aggregated amyloid β protein is peripherally administered to a subject, whereby the aggregated amyloid β protein in the brain of the subject can be reduced so that it can be expected to treat Alzheimer's disease. Furthermore, it can be expected to treat (relieve, improve, repair, etc.) genetic defects (including congenital or acquired) in nerve cells, using the rAAV virion of the present invention.

5. Kit of the Present Invention

In a still another embodiment, the present invention provides a kit for producing the rAAV of the present invention. The kit may comprise, for example, (a) a first polynucleotide and (b) a second polynucleotide as described above. The first polynucleotide may contain, e.g., a polynucleotide encoding the protein of SEQ ID NOs: 8, 10 and 12. The second polynucleotide may or may not contain a therapeutic gene of interest, and preferably may contain various restriction enzyme cleavage sites used to incorporate such a therapeutic gene of interest.

The kit for producing the rAAV virion of the present invention further comprises any component described herein (e.g., an AdV helper, etc.). The kit of the present invention may further include instructions describing the protocols for producing the rAAV virion using the kit of the present invention.

Unless otherwise specified, all terms used herein are intended to refer to ordinary meanings as are generally understood by those skilled in the art.

EXAMPLES

The present invention is described below in more detail by referring to Examples but the scope of the invention should not be limited to the following Examples.

Materials and Methods (1) Modification of AAV Coat (Capsid) Protein VP1

For 3 types of AAV, i.e., AAV serotype 1 (AAV1), AAV serotype 2 (AAV2) and AAV serotype 9 (AAV9), plasmids pAAV1-RC, pAAV2-RC and pAAV9-RC containing the nucleotide sequences encoding the respective VP1 capsid proteins were used as templates. These plasmids are derived from AAV3 Rep/VP described in the publication (Handa, et al., J Gen Virol, 81: 2077-2084, 2000) and contain the AAV3 Rep sequence (Muramatsu, et al., Virology 221, 208-217 (1996)). These nucleotide sequences of AAV VP1 were already reported to GenBank under Accession Nos. AF063497, AF043303 and AY530579, respectively (set forth in SEQ ID NOs: 1, 3 and 5, respectively). The primers shown below were synthesized, and the tyrosine (Y) residues were substituted with phenylalanine (F) residues which were located at position 445 of the AAV1 VP1 amino acid sequence (SEQ ID NO: 2), at position 444 of the AAV2 VP1 amino acid sequence (SEQ ID NO: 4) and at position 446 of the AAV9 VP1 amino acid sequence (SEQ ID NO: 6), using a Quick Change II XL site-directed mutagenesis kit (Stratagene). Plasmids pAAV1-yfRC, pAAV2-yfRC and pAAV9-yfRC containing the polynucleotides encoding the substituted amino acid sequences AAV1-yfVP1 (SEQ ID NO: 8), AAV2-yfVP1 (SEQ ID NO: 10) and AAV9-yfVP1-3 (SEQ ID NO: 12), respectively, were prepared. The plasmids pAAV1-yfRC, pAAV2-yfRC and pAAV9-yfRC all contained the nucleotide sequence (SEQ ID NO: 15) encoding AAV2 Rep.

```
                                           (SEQ ID NO: 17)
yfAAV1-F: 5'-CGACCAATACCTGTATTTCCTGAACAGAACTC-3'

(SEQ ID NO: 18)
yfAAV1-R: 3'-GCTGGTTATGGACATAAAGGACTTGTCTTGAG-5'

(SEQ ID NO: 19)
yfAAV2-F: 5'-CGACCAGTACCTGTATTTCTTGAGCAGAACAAAC-3'

(SEQ ID NO: 20)
yfAAV2-R: 3'-GCTGGTCATGGACATAAAGAACTCGTCTTGTTTG-5'

(SEQ ID NO: 21)
yfAAV9-F: 5'-CGACCAATACTTGTACTTTCTCTCAAAGAC-3'

(SEQ ID NO: 22)
yfAAV9-R: 3'-GCTGGTTATGAACATGAAAGAGAGTTTCTG-5'
```

(2) Production of rAAV Vector (a) Production of Vector Genome Plasmid

Synapsin I (SynI) promoter (GenBank Accession No. M55300.1, SEQ ID NO: 23) was used as a nerve cell-specific promoter, or myelin basic protein (MBP) promoter (GenBank Accession No. M63599, SEQ ID NO: 24) as an oligodendrocyte-specific promoter. Cytomegalovirus enhancer/chicken β-actin (CAG) promoter was used as a control (Niwa H., et al., Gene 108:193-200, 1991). These promoters and the green fluorescence protein (GFP) nucleotide sequence (TAKARA Product Code Z2468N) were inserted between the hairpin DNA sequences, called inverted terminal repeats (ITRs), at the 5' and 3' ends of the plasmid pAAV3 containing the AAV serotype 3 (AAV3) DNA sequence, constructing three plasmids pAAV-SynI-GFP, pAAV-MBP-GFP and pAAV-CAG-GFP. The basic structures of these plasmids are described in Li et al., Mol Ther 13:160-166. 2006.

(b) Transfection to HEK293 Cells

<Day 1>

HEK293 cells of $1.5 \times 10^6$ were plated in a 225 $cm^2$ flask and incubated in 10% FCS-DMEM/F12 medium under 5% $CO_2$ at 37° C.

<Day 3>

Transfection was performed by the calcium phosphate method. The following 10 combinations of the plasmids (AAV vector plasmids+AAV helper plasmids) and the helper plasmids pHelpers containing the adenovirus (AdV) nucleotide sequence (AAV Helper-Free System from Agilent Technologies (Catalog No. 240071)) in an amount of 25 μg each (75 μg in total) were mixed in 0.3M $CaCl_2$.

TABLE 1

| Sample ID | AAV vector genome plasmid | AAV helper plasmid | AdV helper plasmid | produced rAAV virion |
|---|---|---|---|---|
| 1 | pAAV-CAG-GFP1 | pAAV1-RC | pHelper | AAV1-CAG-GFP1 |
| 2 | pAAV-CAG-GFP1 | pAAV1-yfRC | ↑ | yfAAV1-CAG-GFP1 |
| 3 | pAAV-SynI-GFP1 | pAAV1-RC | ↑ | AAV1-SynI-GFP1 |
| 4 | pAAV-SynI-GFP1 | pAAV1-yfRC | ↑ | yfAAV1-SynI-GFP1 |
| 5 | pAAV-SynI-GFP1 | pAAV2-RC | ↑ | AAV2-SynI-GFP1 |
| 6 | pAAV-SynI-GFP1 | pAAV2-yfRC | ↑ | yfAAV2-SynI-GFP1 |
| 7 | pAAV-CAG-GFP1 | pAAV9-RC | ↑ | AAV9-CAG-GFP1 |
| 8 | pAAV-CAG-GFP1 | pAAV9-yfRC | ↑ | yfAAV9-CAG-GFP1 |
| 9 | pAAV-SynI-GFP1 | pAAV9-yfRC | ↑ | yfAAV9-SynI-GFP1 |
| 10 | pAAV-MBP-GFP1 | pAAV9-yfRC | ↑ | yfAAV9-MBP-GFP1 |

Subsequently, 2×HBS (80 mM NaCl, 50 mM Hepes buffer, 1.5 mM $Na_2HPO_4$ (pH7.10)) was added to each mixture to prepare the DNA-calcium phosphate complex. The culture medium in the flask was replaced with the medium supplemented with the DNA-calcium phosphate complex. After incubation for several hours, the medium was exchanged.

<Day 6>

Resultant 10 types of recombinant virus virions ("rAAV virion" in the table above) by the above combinations were recovered. By adding 0.5 mM EDTA, the cells were removed from the culture dish and suspended in TBS (100 mM Tris HCl, pH 8.0, 150 mM NaCl). Freezing/thawing was repeated 3 times using dry ice-ethanol and a water bath at 37° C. to lyse the cells. After centrifugation at 10,000×g for 10 minutes, the supernatant was recovered to remove coarse cell debris.

(c) Purification of Virus Vector

According to the following procedure, cesium chloride CsCl density gradient ultracentrifugation was performed to purify the rAAV vector. CsCl of 1.5 M and 1.25 M was layered in an ultracentrifugation tube to form a density gradient. The rAAV vector-containing cell lysate was layered, followed by ultracentrifugation (30,000 rpm, 2.5 hours). The refractive index was measured and the fraction containing the rAAV vector with RI of 1.365 to 1.380 was recovered. This fraction was layered again over a CsCl solution and ultracentrifuged (36,000 rpm, 2.5 hours) to give the rAAV-containing fraction.

(d) Measurement of Virus Vector Titer (Real Time PCR)

A $10^{-2}$ to $10^{-6}$ dilution series of the purified rAAV was prepared. The primer set (SEQ ID NOS: 25 and 26) containing the GFP sequence as a standard was used for quantification on the Applied Biosystems 7900HT Fast Real Time PCR System (Applied Biosystems).

Example 1

1. Gene Transfer to Nerve Cells in the Brain of Adult Mice (1) Intracardial Administration of rAAV Vector in Mice Animals used were 30 male C57BL6 adult mice at 4 months old after birth (3 mice for each vector). After anesthesia by intraperitoneal administration of 200 µl per 30 g body weight of Nembutal, the mice were fixed on a stereotaxic apparatus for small animals. The mice were injected with each dilution of the above vectors diluted in PBS at $2 \times 10^{12}$ vg (dose volume: 100 µl), using a 1 ml insulin syringe via percutaneous puncture of the left ventricle. The mice were observed in a cage placed on a heating pad until they awoke from anesthesia. Thereafter, the mouse cage was put back in a rack for infected animals.

(2) Immunohistochemistry

Under deep anesthesia, mice were infused with PBS and then with ice-chilled 4% PFA. The brain and spinal cord were dissected and then postfixed for 4 hours in 4% PFA. A slice (40 µm) of brain coronal sections in the range (3.2 mm) from 0.7 mm anterior to 2.5 mm posterior from the bregma was prepared. Also, a slice (40 µm) of horizontal cross section of the cervical spinal cord was prepared. Blocking was performed for 1 hour in 0.3% Triton X-100/PBS containing 2% Mouse IgG Blocking solution (M.O.M Kit; Vector Laboratories, Burlingame, Calif., USA), followed by incubation with NeuN (1:100, mouse anti-Neuronal nuclei monoclonal antibody; Chemicon, Temecula, Calif., USA) and GFP (1:1000, rabbit anti-GFP polyclonal antibody; Abcam, Cambridge, Mass., USA) overnight at 4° C. Subsequently, the slices were incubated with Alexa Fluor (registered trademark) 594 anti-mouse IgG and then with Alexa Fluor (registered trademark) 488 anti-rabbit IgG (1:500, Invitrogen, Carlsbad, Calif., USA) at room temperature for 2 hours to visualize them. Observation was performed under a confocal laser microscope (TCS NT; Leica, Heidelberg, Germany) to count GFP and NeuN-positive cells per 0.04 mm³ in the cerebral cortices (1 m×1 mm×40 µm) in slices at 200 µm intervals and per spinal cord slice. Also, GFP-positive cells in the spinal cord were identified by GFP/ChAT double immunofluorescence staining described below. After blocking in a similar manner, a slice of the cervical spinal cord was incubated with ChAT (diluted in 1:100, mouse anti-ChAT polyclonal antibody; Chemicon, Temecula, Calif., USA) and GFP (diluted in 1:1000, Abcam) at 4° C. overnight. Thereafter, the slice was incubated with Alexa Fluor (registered trademark) 594 anti-mouse IgG and then with Alexa Fluor (registered trademark) 488 anti-rabbit IgG (1:500, Invitrogen) at room temperature for 2 hours to visualize them. The slice was then observed as in the GFP/NeuN double staining.

For GFP/Olig2 double immunofluorescence staining, the slice was blocked in 0.3% TritonX-100/PBS containing 3% goat serum, followed by incubation with Olig2 (diluted in 1:50, rabbit anti-Olig2 polyclonal antibody; IBL, Takasaki, Gunma, Japan) at 4° C. overnight. Thereafter, the slice was incubated with Alexa Fluor (registered trademark) 594 anti-mouse IgG and then with Alexa Fluor (registered trademark) 488 anti-rabbit IgG (diluted in 1:500, Invitrogen) at room temperature for 2 hours, respectively. Observation was performed as in the other immunofluorescent staining to count the cells emitting fluorescence.

2. Results (1) Among the combinations shown in TABLE 1 above, no GFP expression was observed in nerve cells of the cerebral cortex and spinal cord in the combinations that produced the following 6 species of rAAV vectors.

AAV1-CAG-GFP (Sample ID: 1),
yfAAV1-CAG-GFP (Sample ID: 2),
AAV1-SynI-GFP (Sample ID: 3),
AAV2-SynI-GFP (Sample ID: 5),
yfAAV2-SynI-GFP (Sample ID: 6),
AAV9-CAG-GFP (Sample ID: 7).

(2) In the combination of yfAAV1-SynI-GFP (Sample ID: 4), the GFP expression was observed in nerve cells of the brain and spinal cord, while no positive cells were detected with the combination of AAV1-SynI-GFP (Sample ID: 3) (FIG. 1). The results thus revealed that highly efficient gene transfer into nerve cells in the brain can be achieved by replacing tyrosine (Y) 445 in the capsid protein VP1 of AAV1 with phenylalanine (F).

(3) In yfAAV9-CAG-GFP (Sample ID: 8), a few nerve cells were observed to express GFP, while most of the GFP-positive cells were glial cells, not nerve cells. In contrast, in yfAAV9-SynI-GFP (Sample ID: 9), approximately 4-fold higher counts of the GFP-positive nerve cells were seen (FIGS. 2A and 2B and FIG. 3). In yfAAV9-MBP-GFP, many GFP-positive oligodendrocytes were seen (FIG. 2C). The results thus indicate that highly efficient gene transfer into nerve cells in the brain by peripheral administration of the rAAV vector can be achieved by using the nerve cell-specific promoter or oligodendrocyte-specific promoter sequence.

When the rAAV virion was not administered peripherally but was injected directly into the brain, transduction efficiencies into nerve cells are sufficiently high even in case that the CAG promoter was used; it was specifically shown that the gene expression level was 2 to 4 times larger than Syn I promoter (Hioki et al., Gene Ther 14: 872-882, 2007, etc.). However, when the rAAV virion of the present invention was intravascularly administered, most of the gene expression was found in glia-like cells, not in nerve cells, for the rAAV virion where the CAG promoter was used. Also when the rAAV vector in which the conventional CMV promoter was used, the gene was introduced mostly in glia-like cells, not in nerve cells, in the adult.

Meanwhile, the gene expression level of nerve cell-specific promoter SynI in nerve cells was more prominent than that of the CAG promoter. Accordingly, the results above demonstrate that nerve cell-specific promoters such as SynI, etc. are more advantageous as a promoter used in combination with the rAAV virion of the present invention rather than generally strong, non-specific promoters such as the CAG promoter, etc., and show synergistic effects on gene transfer into nerve cells through peripheral administration in these combinations.

In the spinal cord, 24±3.5 of nerve cells per slice of the cervical spinal cord in which GFP and NeuN were positive were observed. In addition, 4 to 5 cells in the GFP-positive cells in each slice were ChAT-positive motor nerve cells (FIG. 4). Accordingly, the results demonstrate that by using the nerve cell-specific promoter (SynI) or oligodendrocyte-specific promoter (MBP), the gene can be stably transferred to nerve cells and oligodendrocytes in the adult mouse brain and spinal cord through peripheral administration.

3. Summary

Based on the foregoing results, it was demonstrated that by substituting the tyrosine (Y) residue at each of positions 445/444/446 in the wild type AAV1/2/9 capsid VP1 protein, respectively, with a phenylalanine (F) residue and by using the SynI promoter sequence or MBP promoter sequence as a nerve cell-specific promoter in combination with a therapeutic gene of interest, the rAAV vector of the present invention was able to pass through the blood-brain barrier through peripheral administration to adult mice and finally transfer the gene to nervous system cells in the brain and spinal cord with a high efficiency.

Example 2

Gene Transfer to Fetal Brain Through Peripheral Administration to Mother Mice

It is reported that a gene was transferred to fetal mice by intraamniotically administering the rAAV vector to mother mice (RAHIM ET AL., FASEB Journal, pp 1-14, Vol. 25 Oct. 2011). Therefore, gene transfer to fetal mice by peripheral administration of the rAAV vector of the present invention to mother mice was examined Materials and Methods
rAAV Vector: yfAAV9-SynI-AcGFP1 (Sample ID: 9)
Titer: $1.3 \times 10^{13}$ vector genome/ml
Dosing Volume: 50 µl
Method of Administration On Day 13 of pregnancy, the rAAV vector above was given to mother mice (3) by intracardial administration. For their offspring mice (9 in total), the coronal section slices (40 µm thick) from the area around the hippocampus of each brain on Day 1 and Weeks 3, 4 and 11 after birth were prepared through infusion and fixation with 4% paraformaldehyde (PFA). GFP expressed in nerve cells in each of the sliced specimens prepared was detected, as described above.

Results

In 20 sliced specimens in total from the 5 mice, expressed GFP was assayed; 4.6 cells/slice on average were observed to be GFP-positive (FIG. 5). The results reveal that the rAAV vector of the present invention was able to transfer the gene to nerve cells in the fetal brain even through peripheral administration to the mother mice.

Example 3

Expression Regulation by Aromatic Amino Acid Decarboxylase (AADC) In Brain Nerve Cells Using the Recombinant AAV Vector: yfAAV9-SynI-GFP-miAADC It was investigated to determine if the rAAV vector of the present invention is useful as a therapeutic vector that can regulate the expression of endogenous gene, by incorporating miRNA, etc. into viral genome. Specific procedures are as follows: an rAAV vector was constructed from yfAAV9-SynI-GFP (Sample ID: 9) as a basis to contain yfAAV9 as a capsid protein and express miRNA against mouse aromatic amino acid decarboxylase (AADC) and green fluorescent protein (GFP) by nerve cell-specific Synapsin I promoter. The vector was given to mice and examined if the vector could decrease AADC in the brain nerve cells.

For the miRNA used, the sequence described below was synthesized to obtain 5'-TGCCTTTATGTCCTGAATT-3' (SEQ ID NO: 27) corresponding to the nucleotide positions 831 to 851 of mouse AADC (GenBank accession No. NM_016672).

(SEQ ID NO: 28)
5'-GAATTCAGGACAGATAAAGGCAGTTTTGGCCACTGACTGACTGCCTT

TATGTCCTGAATT-3'

This sequence was incorporated into the downstream of GFP gene in the rAAV vector genome plasmid pAAV-SynI-GFP designated as Sample ID: 9 in TABLE 1 above to construct pAAV-SynI-GFP-miAADC (cf., SEQ ID NO: 29). As in Sample ID: 9, both the AAV helper plasmid pAAV9-yfRC and AdV helper plasmid pHelper were used together to construct the rAAV virion yfAAV9-SynI-GFP-miAADC.

Materials and Procedures
rAAV Vector: yfAAV9-SynI-GFP-miAADC
Titer: $1.7 \times 10^{14}$ vector genome/ml
Adult mice: C57BL/6J, 10 weeks old, 4 male mice
Intracardial administration: 50 µl/mouse
Procedures for Brain Tissue Analysis The mice were infused and fixed with 4% paraformaldehyde (PFA) 2 weeks after administration of the rAAV vector. The brain was then removed and fixed for 4 hours followed by 10%→20%→30% sucrose, preparing coronal section slices of 40 µm thick on slide glasses. For immunostaining, the sliced specimen was blocked with 3% normal goat serum. Then, rabbit anti-AADC (anti-AADC, diluted to 1:5000, provided with courtesy by Dr. Toshiharu Nagatsu, Nagoya University) and murine anti-tyrosine hydroxylase (anti-TH) (Dia Sorin, diluted to 1:800) as primary antibodies were reacted with the sliced specimen at 4° C. overnight. Secondary antibodies including Alexa Fluor (registered trademark) 594 anti-rabbit IgG and Alexa Fluor (registered trademark) 405 anti-mouse IgG (both from Life Technologies, diluted to 1:1000) were both reacted with each sliced specimen at room temperature for 2 hours. Thereafter, this antibody was reacted with each sliced specimen at room temperature for an hour, using Alexa Fluor (registered trademark) 488 conjugate anti-GFP (Life Technologies, diluted to 1:400). The respective fluorescent substances in the sliced specimens were visualized by a confocal laser scanning microscope (FV10i; Olympus, Tokyo) (FIG. 6).

Results

In FIG. 6, left (anti-GFP), 5 GFP-positive cells were observed in the substantia nigra pars compacta. It is thus confirmed that the rAAV vector of the present invention was able to transfer the gene to the nerve cells as in the Examples above. The results from these nerve cells reacted with anti-AADC exhibited almost the same reaction as the background; the cells were not significantly colored (FIG. 5, center, anti-AADC). Consequently, the expression of AADC in the brain nerve cells was significantly decreased by using the rAAV vector of the present invention. For control, it was confirmed that expression of intracellular protein tyrosine hydroxylase (TH) was maintained (FIG. 5, right, anti-TH). Based on the foregoing, the results showed that the rAAV vector of the present invention is capable of transferring genes to nerve cells in the brain and thus is useful as a therapeutic vector by introducing miRNA into viral genome to suppress the expression of endogenous genes, or the like.

INDUSTRIAL APPLICABILITY

The recombinant adeno-associated virus (rAAV) virion of the present invention is capable of passing through the blood-brain barrier and thus capable of transferring genes to nervous system cells through easy administration means including peripheral administration. Therefore, the pharmaceutical composition capable of gene transfer into nervous system cells can be provided by incorporating the polynucleotide encoding a useful protein including, e.g., an antibody and a neurotropic factor into the present recombinant vector. The recombinant vector of the present invention, in which a gene encoding, e.g., an antibody against amyloid 13 protein aggregate as the cause of Alzheimer's disease is incorporated, can provide a safer therapeutic means for Alzheimer's disease. The viral particles for introducing a gene of interest into nervous system cells can be produced by using the method for preparing viral particles of the present invention and/or the kit of the present invention.

SEQUENCE LISTING FREE TEXT

SEQ ID NO: 1 Wild-type AAV1-derived capsid protein AAV1-VP1 nucleotide sequence (GenBank: NC_002077.1)
SEQ ID NO: 2 Wild-type AAV1-derived capsid protein AAV1-VP1 amino acid sequence (GenBank: NC_2077.1)
SEQ ID NO: 3 Wild-type AAV2-derived capsid protein AAV2-VP1 nucleotide sequence (GenBank: NC_001401.2)
SEQ ID NO: 4 Wild-type AAV2-derived capsid protein AAV2-VP1 amino acid sequence (GenBank: NC_001401.2)
SEQ ID NO: 5 Wild-type AAV9-derived capsid protein AAV9-VP1 nucleotide sequence (GenBank: AY530579.1)
SEQ ID NO: 6 Wild-type AAV9-derived capsid protein AAV9-VP1 amino acid sequence (GenBank: AY530579.1)
SEQ ID NO: 7 AAV1-derived capsid protein mutant AAV1-yfVP1 nucleotide sequence
SEQ ID NO: 8 AAV1-derived capsid protein mutant AAV1-yfVP1 amino acid sequence
SEQ ID NO: 9 AAV2-derived capsid protein mutant AAV2-yfVP1 nucleotide sequence
SEQ ID NO: 10 AAV2-derived capsid protein mutant AAV2-yfVP1 amino acid sequence
SEQ ID NO: 11 AAV9-derived capsid protein mutant AAV9-yfVP1 nucleotide sequence
SEQ ID NO: 12 AAV9-derived capsid protein mutant AAV9-yfVP1 amino acid sequence
SEQ ID NO: 13 AAV3-derived 5' end ITR nucleotide sequence (GenBank NC_001729-derived)
SEQ ID NO: 14 AAV3-derived 3' end ITR nucleotide sequence
SEQ ID NO: 15 AAV2-derived rep gene nucleotide sequence
SEQ ID NO: 16 AAV2-derived Rep protein amino acid sequence
SEQ ID NO: 17 Mutagenesis primer 1 (yfAAV1-F) nucleotide sequence
SEQ ID NO: 18 Mutagenesis primer 2 (yfAAV1-R) nucleotide sequence
SEQ ID NO: 19 Mutagenesis primer 3 (yfAAV2-F) nucleotide sequence
SEQ ID NO: 20 Mutagenesis primer 4 (yfAAV2-R) nucleotide sequence
SEQ ID NO: 21 Mutagenesis primer 5 (yfAAV9-F) nucleotide sequence
SEQ ID NO: 22 Mutagenesis primer 6 (yfAAV9-R) nucleotide sequence
SEQ ID NO: 23 Synapsin I promoter sequence (GenBank: M55300.1)
SEQ ID NO: 24 Myelin basic protein promoter sequence (GenBank: M63599 (human)-derived)
SEQ ID NO: 25 GFP detection primer 1 nucleotide sequence
SEQ ID NO: 26 GFP detection primer 2 nucleotide sequence
SEQ ID NO: 27 Nucleotide sequence designed for 831-851 nucleotides of murine aromatic amino acid decarboxylase (AADC: GenBank accession No. NM_016672)
SEQ ID NO: 28 Nucleotide sequence to form miRNA against murine aromatic amino acid decarboxylase (AADC)
SEQ ID NO: 29 Nucleotide sequence to express GFP and miRNA (SEQ ID NO: 28) against murine aromatic amino acid decarboxylase (AADC)

The invention claimed is:

1. A method of delivering a therapeutic gene of interest to a nerve cell in a brain of a living subject, comprising:
providing a recombinant adeno-associated virus (rAAV) vector, and
peripherally administering said rAAV vector to a subject; wherein said rAAV vector is configured to pass through an adult, fetus or neonate blood-brain barrier to deliver a therapeutic gene of interest to a nerve cell in a brain of a living subject, and comprises:
(a) a capsomere which comprises a protein comprising the amino acid sequence of SEQ ID NO: 8 or 12, wherein the protein is capable of forming a virus virion, and
(b) a polynucleotide packaged in said capsomere, the polynucleotide comprising a nervous system cell-specific promoter sequence and a nucleotide sequence as a gene operably linked to the promoter sequence, wherein the promoter sequence is selected from the group consisting of (i) a synapsin I promoter sequence, (ii) a myelin basic protein promoter sequence, and (iii) a L7 promoter sequence that is a cerebellar Purkinje cell specific promoter sequence;
said recombinant adeno-associated virus vector is not self-complementary (sc); and
said peripherally administering is not to blood vessels in the head of the subject.

2. The method according to claim 1, wherein the 5' end of the polynucleotide comprises a 5' end-inverted terminal repeat (ITR) sequence derived from adeno-associated virus serotype 1 (AAV1), serotype 2 (AAV2), serotype 3 (AAV3), serotype 4 (AAV4) or serotype 9 (AAV9), and the 3' end of the polynucleotide comprises a 3' end-ITR sequence derived from AAV1, AAV2, AAV3, AAV4, or AAV9.

3. The method according to claim 1, wherein the 5' and 3' ends of the polynucleotide comprise the nucleotide sequences of SEQ ID NO: 13 and SEQ ID NO: 14, respectively.

4. The method according to claim 1, wherein the polynucleotide has a full length of 2 to 6 kb and is a single stranded DNA which is a sense strand or an antisense strand.

5. The method according to claim 4, wherein the promoter sequence comprises the polynucleotide of SEQ ID NO: 23 or SEQ ID NO: 24.

6. The method according to claim 4, wherein the nucleotide sequence operably linked to the promoter sequence encodes a protein selected from the group consisting of an antibody, a nerve growth factor (NGF), a growth factor, an acidic fibroblast growth factor (aFGF), a basic fibroblast growth factor (bFGF), a glial cell line-derived neurotrophic factor (GDNF), an aromatic amino acid decarboxylase, and an amyloid 13 degrading protease that is Neprilysin.

7. The method according to claim 4, wherein the nucleotide sequence operably linked to the promoter sequence expresses dsRNA, siRNA, shRNA or miRNA to downregulate expression of an aromatic amino acid decarboxylase or α-synuclein.

8. The method according to claim 6, wherein the antibody is an antibody that binds to aggregated amyloid 13 protein.

9. The method according to claim 1, wherein the living subject is human.

10. The method according to claim 1, wherein the capsomere which comprises the protein comprises the amino acid sequence of SEQ ID NO: 8.

11. The method according to claim 1, wherein the capsomere which comprises the protein comprises the amino acid sequence of SEQ ID NO: 12.

12. The method according to claim 1, wherein the promoter sequence is the synapsin I promoter sequence.

13. The method according to claim 1, wherein the promoter sequence is the myelin basic protein promoter sequence.

14. The method according to claim 1, wherein the peripherally administering is performed by intraarterial administration, intrapericardial administration, intramuscular administration, or umbilical intravascular administration.

15. A method of treating a subject with a neurological disorder, an inborn error of metabolism in a neuron, or a demyelinating disorder in a neuron, comprising delivering a therapeutic gene of interest by the method of claim 1.

16. The method according to claim 15, wherein the neurological disorder, the inborn error of metabolism, or the demyelinating disorder is selected from the group consisting of: Parkinson's disease, Alzheimer's disease, triplet repeat disease, prion disease, amyotrophic lateral sclerosis, spinocerebellar degeneration, channel disease, epilepsy; Wilson's disease, peroxisome disease; and multiple sclerosis.

* * * * *

```
SEQUENCE LISTING

<160> NUMBER OF SEQ ID NOS: 29

<210> SEQ ID NO 1
<211> LENGTH: 2208
<212> TYPE: DNA
<213> ORGANISM: adeno-associated virus 1
<220> FEATURE:
<221> NAME/KEY: CDS
<222> LOCATION: (1)..(2208)
<223> OTHER INFORMATION: AAV1-VP1 Capsid

<400> SEQUENCE: 1 atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aag ccc      96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60
```

```
gtc aac gcg gcg gac gca gcg gcc ctc gag cac gac aag gcc tac gac    240
Val Asn Ala Ala Asp Ala Ala Ala Leu Glu His Asp Lys Ala Tyr Asp
 65              70                  75                  80 cag cag ctc aaa gcg ggt gac aat ccg tac ctg cgg tat aac cac gcc    288
Gln Gln Leu Lys Ala Gly Asp Asn Pro Tyr Leu Arg Tyr Asn His Ala
             85                  90                  95 gac gcc gag ttt cag gag cgt ctg caa gaa gat acg tct ttt ggg ggc    336
Asp Ala Glu Phe Gln Glu Arg Leu Gln Glu Asp Thr Ser Phe Gly Gly
                100                 105                 110 aac ctc ggg cga gca gtc ttc cag gcc aag aag cgg gtt ctc gaa cct    384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aaa cgt    432
Leu Gly Leu Val Glu Glu Gly Ala Lys Thr Ala Pro Gly Lys Lys Arg
130                 135                 140 ccg gta gag cag tcg cca caa gag cca gac tcc tcc tcg ggc atc ggc    480
Pro Val Glu Gln Ser Pro Gln Glu Pro Asp Ser Ser Ser Gly Ile Gly
145                 150                 155                 160 aag aca ggc cag cag ccc gct aaa aag aga ctc aat ttt ggt cag act    528
Lys Thr Gly Gln Gln Pro Ala Lys Lys Arg Leu Asn Phe Gly Gln Thr
                165                 170                 175 ggc gac tca gag tca gtc ccc gat cca caa cct ctc gga gaa cct cca    576
Gly Asp Ser Glu Ser Val Pro Asp Pro Gln Pro Leu Gly Glu Pro Pro
        180                 185                 190 gca acc ccc gct gct gtg gga cct act aca atg gct tca ggc ggt ggc    624
Ala Thr Pro Ala Ala Val Gly Pro Thr Thr Met Ala Ser Gly Gly Gly
                195                 200                 205 gca cca atg gca gac aat aac gaa ggc gcc gac gga gtg ggt aat gcc    672
Ala Pro Met Ala Asp Asn Asn Glu Gly Ala Asp Gly Val Gly Asn Ala
210                 215                 220 tca gga aat tgg cat tgc gat tcc aca tgg ctg ggc gac aga gtc atc    720
Ser Gly Asn Trp His Cys Asp Ser Thr Trp Leu Gly Asp Arg Val Ile
225                 230                 235                 240 acc acc agc acc cgc acc tgg gcc ttg ccc acc tac aat aac cac ctc    768
Thr Thr Ser Thr Arg Thr Trp Ala Leu Pro Thr Tyr Asn Asn His Leu
                245                 250                 255 tac aag caa atc tcc agt gct tca acg ggg gcc agc aac gac aac cac    816
Tyr Lys Gln Ile Ser Ser Ala Ser Thr Gly Ala Ser Asn Asp Asn His
                260                 265                 270 tac ttc ggc tac agc acc ccc tgg ggg tat ttt gat ttc aac aga ttc    864
Tyr Phe Gly Tyr Ser Thr Pro Trp Gly Tyr Phe Asp Phe Asn Arg Phe
        275                 280                 285 cac tgc cac ttt tca cca cgt gac tgg cag cga ctc atc aac aac aat    912
His Cys His Phe Ser Pro Arg Asp Trp Gln Arg Leu Ile Asn Asn Asn
    290                 295                 300 tgg gga ttc cgg ccc aag aga ctc aac ttc aaa ctc ttc aac atc caa    960
Trp Gly Phe Arg Pro Lys Arg Leu Asn Phe Lys Leu Phe Asn Ile Gln
305                 310                 315                 320 gtc aag gag gtc acg acg aat gat ggc gtc aca acc atc gct aat aac   1008
Val Lys Glu Val Thr Thr Asn Asp Gly Val Thr Thr Ile Ala Asn Asn
                325                 330                 335 ctt acc agc acg gtt caa gtc ttc tcg gac tcg gag tac cag ctt ccg   1056
Leu Thr Ser Thr Val Gln Val Phe Ser Asp Ser Glu Tyr Gln Leu Pro
                340                 345                 350 tac gtc ctc ggc tct gcg cac cag ggc tgc ctc cct ccg ttc ccg gcg   1104
Tyr Val Leu Gly Ser Ala His Gln Gly Cys Leu Pro Pro Phe Pro Ala
        355                 360                 365 gac gtg ttc atg att ccg caa tac ggc tac ctg acg ctc aac aat ggc   1152
Asp Val Phe Met Ile Pro Gln Tyr Gly Tyr Leu Thr Leu Asn Asn Gly
```

```
            370                 375                 380
agc caa gcc gtg gga cgt tca tcc ttt tac tgc ctg gaa tat ttc cct       1200
Ser Gln Ala Val Gly Arg Ser Ser Phe Tyr Cys Leu Glu Tyr Phe Pro
385                 390                 395                 400 tct cag atg ctg aga acg ggc aac aac ttt acc ttc agc tac acc ttt       1248
Ser Gln Met Leu Arg Thr Gly Asn Asn Phe Thr Phe Ser Tyr Thr Phe
            405                 410                 415 gag gaa gtg cct ttc cac agc agc tac gcg cac agc cag agc ctg gac       1296
Glu Glu Val Pro Phe His Ser Ser Tyr Ala His Ser Gln Ser Leu Asp
                420                 425                 430 cgg ctg atg aat cct ctc atc gac caa tac ctg tat tac ctg aac aga       1344
Arg Leu Met Asn Pro Leu Ile Asp Gln Tyr Leu Tyr Tyr Leu Asn Arg
            435                 440                 445 act caa aat cag tcc gga agt gcc caa aac aag gac ttg ctg ttt agc       1392
Thr Gln Asn Gln Ser Gly Ser Ala Gln Asn Lys Asp Leu Leu Phe Ser
450                 455                 460 cgt ggg tct cca gct ggc atg tct gtt cag ccc aaa aac tgg cta cct       1440
Arg Gly Ser Pro Ala Gly Met Ser Val Gln Pro Lys Asn Trp Leu Pro
465                 470                 475                 480 gga ccc tgt tat cgg cag cag cgc gtt tct aaa aca aaa aca gac aac       1488
Gly Pro Cys Tyr Arg Gln Gln Arg Val Ser Lys Thr Lys Thr Asp Asn
                485                 490                 495 aac aac agc aat ttt acc tgg act ggt gct tca aaa tat aac ctc aat       1536
Asn Asn Ser Asn Phe Thr Trp Thr Gly Ala Ser Lys Tyr Asn Leu Asn
            500                 505                 510 ggg cgt gaa tcc atc atc aac cct ggc act gct atg gcc tca cac aaa       1584
Gly Arg Glu Ser Ile Ile Asn Pro Gly Thr Ala Met Ala Ser His Lys
            515                 520                 525 gac gac gaa gac aag ttc ttt ccc atg agc ggt gtc atg att ttt gga       1632
Asp Asp Glu Asp Lys Phe Phe Pro Met Ser Gly Val Met Ile Phe Gly
530                 535                 540 aaa gag agc gcc gga gct tca aac act gca ttg gac aat gtc atg att       1680
Lys Glu Ser Ala Gly Ala Ser Asn Thr Ala Leu Asp Asn Val Met Ile
545                 550                 555                 560 aca gac gaa gag gaa att aaa gcc act aac cct gtg gcc acc gaa aga       1728
Thr Asp Glu Glu Glu Ile Lys Ala Thr Asn Pro Val Ala Thr Glu Arg
                565                 570                 575 ttt ggg acc gtg gca gtc aat ttc cag agc agc agc aca gac cct gcg       1776
Phe Gly Thr Val Ala Val Asn Phe Gln Ser Ser Ser Thr Asp Pro Ala
            580                 585                 590 acc gga gat gtg cat gct atg gga gca tta cct ggc atg gtg tgg caa       1824
Thr Gly Asp Val His Ala Met Gly Ala Leu Pro Gly Met Val Trp Gln
            595                 600                 605 gat aga gac gtg tac ctg cag ggt ccc att tgg gcc aaa att cct cac       1872
Asp Arg Asp Val Tyr Leu Gln Gly Pro Ile Trp Ala Lys Ile Pro His
610                 615                 620 aca gat gga cac ttt cac ccg tct cct ctt atg ggc ggc ttt gga ctc       1920
Thr Asp Gly His Phe His Pro Ser Pro Leu Met Gly Gly Phe Gly Leu
625                 630                 635                 640 aag aac ccg cct cct cag atc ctc atc aaa aac acg cct gtt cct gcg       1968
Lys Asn Pro Pro Pro Gln Ile Leu Ile Lys Asn Thr Pro Val Pro Ala
                645                 650                 655 aat cct ccg gcg gag ttt tca gct aca aag ttt gct tca ttc atc acc       2016
Asn Pro Pro Ala Glu Phe Ser Ala Thr Lys Phe Ala Ser Phe Ile Thr
            660                 665                 670 caa tac tcc aca gga caa gtg agt gtg gaa att gaa tgg gag ctg cag       2064
Gln Tyr Ser Thr Gly Gln Val Ser Val Glu Ile Glu Trp Glu Leu Gln
            675                 680                 685 aaa gaa aac agc aag cgc tgg aat ccc gaa gtg cag tac aca tcc aat       2112
```

```
Lys Glu Asn Ser Lys Arg Trp Asn Pro Glu Val Gln Tyr Thr Ser Asn
        690                 695                 700 tat gca aaa tct gcc aac gtt gat ttt act gtg gac aac aat gga ctt    2160
Tyr Ala Lys Ser Ala Asn Val Asp Phe Thr Val Asp Asn Asn Gly Leu
705                 710                 715                 720 tat act gag cct cgc ccc att ggc acc cgt tac ctt acc cgt ccc ctg    2208
Tyr Thr Glu Pro Arg Pro Ile Gly Thr Arg Tyr Leu Thr Arg Pro Leu
            725                 730                 735

<210> SEQ ID NO 2
<211> LENGTH: 736
<212> TYPE: PRT
<213> ORGANISM: adeno-associated virus 1

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320
```

-continued

Val Lys Glu Val Thr Thr Asn Asp Gly Val Thr Thr Ile Ala Asn Asn
              325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

-continued

```
<210> SEQ ID NO 3
<211> LENGTH: 2205
<212> TYPE: DNA
<213> ORGANISM: adeno-associated virus 2
<220> FEATURE:
<221> NAME/KEY: CDS
<222> LOCATION: (1)..(2205)
<223> OTHER INFORMATION: AAV2-VP1 Capsid

<400> SEQUENCE: 3 atg gct gcc gat ggt tat ctt cca gat tgg ctc gag gac act ctc tct      48
Met Ala Ala Asp Gly Tyr Leu Pro Asp Trp Leu Glu Asp Thr Leu Ser
1               5                   10                  15 gaa gga ata aga cag tgg tgg aag ctc aaa cct ggc cca cca cca cca      96
Glu Gly Ile Arg Gln Trp Trp Lys Leu Lys Pro Gly Pro Pro Pro Pro
            20                  25                  30 aag ccc gca gag cgg cat aag gac gac agc agg ggt ctt gtg ctt cct     144
Lys Pro Ala Glu Arg His Lys Asp Asp Ser Arg Gly Leu Val Leu Pro
        35                  40                  45 ggg tac aag tac ctc gga ccc ttc aac gga ctc gac aag gga gag ccg     192
Gly Tyr Lys Tyr Leu Gly Pro Phe Asn Gly Leu Asp Lys Gly Glu Pro
 50                  55                  60 gtc aac gag gca gac gcc gcg gcc ctc gag cac gac aaa gcc tac gac     240
Val Asn Glu Ala Asp Ala Ala Ala Leu Glu His Asp Lys Ala Tyr Asp
65                  70                  75                  80 cgg cag ctc gac agc gga gac aac ccg tac ctc aag tac aac cac gcc     288
Arg Gln Leu Asp Ser Gly Asp Asn Pro Tyr Leu Lys Tyr Asn His Ala
                85                  90                  95 gac gcg gag ttt cag gag cgc ctt aaa gaa gat acg tct ttt ggg ggc     336
Asp Ala Glu Phe Gln Glu Arg Leu Lys Glu Asp Thr Ser Phe Gly Gly
            100                 105                 110 aac ctc gga cga gca gtc ttc cag gcg aaa aag agg gtt ctt gaa cct     384
Asn Leu Gly Arg Ala Val Phe Gln Ala Lys Lys Arg Val Leu Glu Pro
        115                 120                 125 ctg ggc ctg gtt gag gaa cct gtt aag acg gct ccg gga aaa aag agg     432
Leu Gly Leu Val Glu Glu Pro Val Lys Thr Ala Pro Gly Lys Lys Arg
    130                 135                 140 ccg gta gag cac tct cct gtg gag cca gac tcc tcc tcg gga acc gga     480
Pro Val Glu His Ser Pro Val Glu Pro Asp Ser Ser Ser Gly Thr Gly
145                 150                 155                 160 aag gcg ggc cag cag cct gca aga aaa aga ttg aat ttt ggt cag act     528
Lys Ala Gly Gln Gln Pro Ala Arg Lys Arg Leu Asn Phe Gly Gln Thr
                165                 170                 175 gga gac gca gac tca gta cct gac ccc cag cct ctc gga cag cca cca     576
Gly Asp Ala Asp Ser Val Pro Asp Pro Gln Pro Leu Gly Gln Pro Pro
            180                 185                 190 gca gcc ccc tct ggt ctg gga act aat acg atg gct aca ggc agt ggc     624
Ala Ala Pro Ser Gly Leu Gly Thr Asn Thr Met Ala Thr Gly Ser Gly
        195                 200                 205 gca cca atg gca gac aat aac gag ggc gcc gac gga gtg ggt aat tcc     672
Ala Pro Met Ala Asp Asn Asn Glu Gly Ala Asp Gly Val Gly Asn Ser
    210                 215                 220 tcg gga aat tgg cat tgc gat tcc aca tgg atg ggc gac aga gtc atc     720
Ser Gly Asn Trp His Cys Asp Ser Thr Trp Met Gly Asp Arg Val Ile
225                 230                 235                 240 acc acc agc acc cga acc tgg gcc ctg ccc acc tac aac aac cac ctc     768
Thr Thr Ser Thr Arg Thr Trp Ala Leu Pro Thr Tyr Asn Asn His Leu
                245                 250                 255 tac aaa caa att tcc agc caa tca gga gcc tcg aac gac aat cac tac     816
Tyr Lys Gln Ile Ser Ser Gln Ser Gly Ala Ser Asn Asp Asn His Tyr
            260                 265                 270
```

|  |  |  |  |  |  |  |  |  |  |  |  |  |  |  |  |
|---|---|---|---|---|---|---|---|---|---|---|---|---|---|---|---|
| ttt | ggc | tac | agc | acc | cct | tgg | ggg | tat | ttt | gac | ttc | aac | aga | ttc | cac | 864 |
| Phe | Gly | Tyr | Ser | Thr | Pro | Trp | Gly | Tyr | Phe | Asp | Phe | Asn | Arg | Phe | His |
|  |  | 275 |  |  |  | 280 |  |  |  | 285 |  |  |  |  | tgc cac ttt tca cca cgt gac tgg caa aga ctc atc aac aac aac tgg     912
Cys His Phe Ser Pro Arg Asp Trp Gln Arg Leu Ile Asn Asn Asn Trp
    290                 295                 300 gga ttc cga ccc aag aga ctc aac ttc aag ctc ttt aac att caa gtc     960
Gly Phe Arg Pro Lys Arg Leu Asn Phe Lys Leu Phe Asn Ile Gln Val
305                 310                 315                 320 aaa gag gtc acg cag aat gac ggt acg acg acg att gcc aat aac ctt    1008
Lys Glu Val Thr Gln Asn Asp Gly Thr Thr Thr Ile Ala Asn Asn Leu
                325                 330                 335 acc agc acg gtt cag gtg ttt act gac tcg gag tac cag ctc ccg tac    1056
Thr Ser Thr Val Gln Val Phe Thr Asp Ser Glu Tyr Gln Leu Pro Tyr
            340                 345                 350 gtc ctc ggc tcg gcg cat caa gga tgc ctc ccg ccg ttc cca gca gac    1104
Val Leu Gly Ser Ala His Gln Gly Cys Leu Pro Pro Phe Pro Ala Asp
        355                 360                 365 gtc ttc atg gtg cca cag tat gga tac ctc acc ctg aac aac ggg agt    1152
Val Phe Met Val Pro Gln Tyr Gly Tyr Leu Thr Leu Asn Asn Gly Ser
    370                 375                 380 cag gca gta gga cgc tct tca ttt tac tgc ctg gag tac ttt cct tct    1200
Gln Ala Val Gly Arg Ser Ser Phe Tyr Cys Leu Glu Tyr Phe Pro Ser
385                 390                 395                 400 cag atg ctg cgt acc gga aac aac ttt acc ttc agc tac act ttt gag    1248
Gln Met Leu Arg Thr Gly Asn Asn Phe Thr Phe Ser Tyr Thr Phe Glu
                405                 410                 415 gac gtt cct ttc cac agc agc tac gct cac agc cag agt ctg gac cgt    1296
Asp Val Pro Phe His Ser Ser Tyr Ala His Ser Gln Ser Leu Asp Arg
            420                 425                 430 ctc atg aat cct ctc atc gac cag tac ctg tat tac ttg agc aga aca    1344
Leu Met Asn Pro Leu Ile Asp Gln Tyr Leu Tyr Tyr Leu Ser Arg Thr
        435                 440                 445 aac act cca agt gga acc acg cag tca agg ctt cag ttt tct cag        1392
Asn Thr Pro Ser Gly Thr Thr Thr Gln Ser Arg Leu Gln Phe Ser Gln
    450                 455                 460 gcc gga gcg agt gac att cgg gac cag tct agg aac tgg ctt cct gga    1440
Ala Gly Ala Ser Asp Ile Arg Asp Gln Ser Arg Asn Trp Leu Pro Gly
465                 470                 475                 480 ccc tgt tac cgc cag cag cga gta tca aag aca tct gcg gat aac aac    1488
Pro Cys Tyr Arg Gln Gln Arg Val Ser Lys Thr Ser Ala Asp Asn Asn
                485                 490                 495 aac agt gaa tac tcg tgg act gga gct acc aag tac cac ctc aat ggc    1536
Asn Ser Glu Tyr Ser Trp Thr Gly Ala Thr Lys Tyr His Leu Asn Gly
            500                 505                 510 aga gac tct ctg gtg aat ccg ggc ccg gcc atg gca agc cac aag gac    1584
Arg Asp Ser Leu Val Asn Pro Gly Pro Ala Met Ala Ser His Lys Asp
        515                 520                 525 gat gaa gaa aag ttt ttt cct cag agc ggg gtt ctc atc ttt ggg aag    1632
Asp Glu Glu Lys Phe Phe Pro Gln Ser Gly Val Leu Ile Phe Gly Lys
    530                 535                 540 caa ggc tca gag aaa aca aat gtg gac att gaa aag gtc atg att aca    1680
Gln Gly Ser Glu Lys Thr Asn Val Asp Ile Glu Lys Val Met Ile Thr
545                 550                 555                 560 gac gaa gag gaa atc agg aca acc aat ccc gtg gct acg gag cag tat    1728
Asp Glu Glu Glu Ile Arg Thr Thr Asn Pro Val Ala Thr Glu Gln Tyr
                565                 570                 575 ggt tct gta tct acc aac ctc cag aga ggc aac aga caa gca gct acc    1776
Gly Ser Val Ser Thr Asn Leu Gln Arg Gly Asn Arg Gln Ala Ala Thr
            580                 585                 590

```
gca gat gtc aac aca caa ggc gtt ctt cca ggc atg gtc tgg cag gac     1824
Ala Asp Val Asn Thr Gln Gly Val Leu Pro Gly Met Val Trp Gln Asp
            595                 600                 605 aga gat gtg tac ctt cag ggg ccc atc tgg gca aag att cca cac acg     1872
Arg Asp Val Tyr Leu Gln Gly Pro Ile Trp Ala Lys Ile Pro His Thr
        610                 615                 620 gac gga cat ttt cac ccc tct ccc ctc atg ggt gga ttc gga ctt aaa     1920
Asp Gly His Phe His Pro Ser Pro Leu Met Gly Gly Phe Gly Leu Lys
625                 630                 635                 640 cac cct cct cca cag att ctc atc aag aac acc ccg gta cct gcg aat     1968
His Pro Pro Pro Gln Ile Leu Ile Lys Asn Thr Pro Val Pro Ala Asn
            645                 650                 655 cct tcg acc acc ttc agt gcg gca aag ttt gct tcc ttc atc aca cag     2016
Pro Ser Thr Thr Phe Ser Ala Ala Lys Phe Ala Ser Phe Ile Thr Gln
        660                 665                 670 tac tcc acg gga cag gtc agc gtg gag atc gag tgg gag ctg cag aag     2064
Tyr Ser Thr Gly Gln Val Ser Val Glu Ile Glu Trp Glu Leu Gln Lys
    675                 680                 685 gaa aac agc aaa cgc tgg aat ccc gaa att cag tac act tcc aac tac     2112
Glu Asn Ser Lys Arg Trp Asn Pro Glu Ile Gln Tyr Thr Ser Asn Tyr
690                 695                 700 aac aag tct gtt aat gtg gac ttt act gtg gac act aat ggc gtg tat     2160
Asn Lys Ser Val Asn Val Asp Phe Thr Val Asp Thr Asn Gly Val Tyr
705                 710                 715                 720 tca gag cct cgc ccc att ggc acc aga tac ctg act cgt aat ctg           2205
Ser Glu Pro Arg Pro Ile Gly Thr Arg Tyr Leu Thr Arg Asn Leu
            725                 730                 735

<210> SEQ ID NO 4
<211> LENGTH: 735
<212> TYPE: PRT
<213> ORGANISM: adeno-associated virus 2

<400> SEQUENCE: 4

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
```

-continued

```
                180                 185                 190
Ala Ala Pro Ser Gly Leu Gly Thr Asn Thr Met Ala Thr Gly Ser Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
```

```
Arg Asp Val Tyr Leu Gln Gly Pro Ile Trp Ala Lys Ile Pro His Thr
    610                 615                 620

Asp Gly His Phe His Pro Ser Pro Leu Met Gly Phe Gly Leu Lys
625                 630                 635                 640

His Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 5
<211> LENGTH: 2208
<212> TYPE: DNA
<213> ORGANISM: adeno-associated virus 9
<220> FEATURE:
<221> NAME/KEY: CDS
<222> LOCATION: (1)..(2208)
<223> OTHER INFORMATION: AAV9-VP1 Capsid

<400> SEQUENCE: 5 atg gct gcc gat ggt tat ctt cca gat tgg ctc gag gac aac ctt agt    48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc    96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg   144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg   192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac   240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc   288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc   336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct   384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg   432
Leu Gly Leu Val Glu Glu Ala Ala Lys Thr Ala Pro Gly Lys Lys Arg
    130                 135                 140 cct gta gag cag tct cct cag gaa ccg gac tcc tcc gcg ggt att ggc   480
Pro Val Glu Gln Ser Pro Gln Glu Pro Asp Ser Ser Ala Gly Ile Gly
145                 150                 155                 160 aaa tcg ggt gca cag ccc gct aaa aag aga ctc aat ttc ggt cag act   528
Lys Ser Gly Ala Gln Pro Ala Lys Lys Arg Leu Asn Phe Gly Gln Thr
```

```
                    165                 170                 175
ggc gac aca gag tca gtc cca gac cct caa cca atc gga gaa cct ccc     576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc     624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc     672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc     720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc     768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac     816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga     864
Ala Tyr Phe Gly Tyr Ser Thr Pro Trp Gly Tyr Phe Asp Phe Asn Arg
        275                 280                 285 ttc cac tgc cac ttc tca cca cgt gac tgg cag cga ctc atc aac aac     912
Phe His Cys His Phe Ser Pro Arg Asp Trp Gln Arg Leu Ile Asn Asn
    290                 295                 300 aac tgg gga ttc cgg cct aag cga ctc aac ttc aag ctc ttc aac att     960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gcc aat    1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc    1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca    1104
Pro Tyr Val Leu Gly Ser Ala His Glu Gly Cys Leu Pro Pro Phe Pro
        355                 360                 365 gcg gac gtt ttc atg att cct cag tac ggg tat ctg acg ctt aat gat    1152
Ala Asp Val Phe Met Ile Pro Gln Tyr Gly Tyr Leu Thr Leu Asn Asp
    370                 375                 380 gga agc cag gcc gtg ggt cgt tcg tcc ttt tac tgc ctg gaa tat ttc    1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag    1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg    1296
Phe Glu Asn Val Pro Phe His Ser Ser Tyr Ala His Ser Gln Ser Leu
            420                 425                 430 gac cga cta atg aat cca ctc atc gac caa tac ttg tac tat ctc tca    1344
Asp Arg Leu Met Asn Pro Leu Ile Asp Gln Tyr Leu Tyr Tyr Leu Ser
        435                 440                 445 aag act att aac ggt tct gga cag aat caa caa acg cta aaa ttc agt    1392
Lys Thr Ile Asn Gly Ser Gly Gln Asn Gln Gln Thr Leu Lys Phe Ser
    450                 455                 460 gtg gcc gga ccc agc aac atg gct gtc cag gga aga aac tac ata cct    1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac    1488
Gly Pro Ser Tyr Arg Gln Gln Arg Val Ser Thr Thr Val Thr Gln Asn
```

```
                Gly Pro Ser Tyr Arg Gln Gln Arg Val Ser Thr Thr Val Thr Gln Asn
                                485                 490                 495 aac aac agc gaa ttt gct tgg cct gga gct tct tct tgg gct ctc aat        1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa        1584
Gly Arg Asn Ser Leu Met Asn Pro Gly Pro Ala Met Ala Ser His Lys
        515                 520                 525 gaa gga gag gac cgt ttc ttt cct ttg tct gga tct tta att ttt ggc        1632
Glu Gly Glu Asp Arg Phe Phe Pro Leu Ser Gly Ser Leu Ile Phe Gly
    530                 535                 540 aaa caa gga act gga aga gac aac gtg gat gcg gac aaa gtc atg ata        1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc        1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag        1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag        1824
Thr Gly Trp Val Gln Asn Gln Gly Ile Leu Pro Gly Met Val Trp Gln
        595                 600                 605 gac aga gat gtg tac ctg caa gga ccc att tgg gcc aaa att cct cac        1872
Asp Arg Asp Val Tyr Leu Gln Gly Pro Ile Trp Ala Lys Ile Pro His
    610                 615                 620 acg gac ggc aac ttt cac cct tct ccg ctg atg gga ggg ttt gga atg        1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg        1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc        2016
Asp Pro Pro Thr Ala Phe Asn Lys Asp Lys Leu Asn Ser Phe Ile Thr
            660                 665                 670 cag tat tct act ggc caa gtc agc gtg gag atc gag tgg gag ctg cag        2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac        2112
Lys Glu Asn Ser Lys Arg Trp Asn Pro Glu Ile Gln Tyr Thr Ser Asn
    690                 695                 700 tat tac aag tct aat aat gtt gaa ttt gct gtt aat act gaa ggt gta        2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg        2208
Tyr Ser Glu Pro Arg Pro Ile Gly Thr Arg Tyr Leu Thr Arg Asn Leu
                725                 730                 735

<210> SEQ ID NO 6
<211> LENGTH: 736
<212> TYPE: PRT
<213> ORGANISM: adeno-associated virus 9

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

```
Gly Tyr Lys Tyr Leu Gly Pro Gly Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
                115                 120                 125
Leu Gly Leu Val Glu Glu Ala Ala Lys Thr Ala Pro Gly Lys Lys Arg
                130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
                210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 7
<211> LENGTH: 2208
<212> TYPE: DNA
<213> ORGANISM: Artificial Sequence
<220> FEATURE:
<223> OTHER INFORMATION: AAV1-yfVP1
<220> FEATURE:
<221> NAME/KEY: CDS
<222> LOCATION: (1)..(2208)
<223> OTHER INFORMATION: AAV1-yfVP1

<400> SEQUENCE: 7

```
atg gct gcc gat ggt tat ctt cca gat tgg ctc gag gac aac ctc tct    48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aag ccc    96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct    144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc    192
Gly Tyr Lys Tyr Leu Gly Pro Phe Asn Gly Leu Asp Lys Gly Glu Pro
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 50  |     |     |     | 55  |     |     |     | 60  |     |     |     |     |     |
| gtc | aac | gcg | gcg | gac | gca | gcg | gcc | ctc | gag | cac | gac | aag | gcc | tac | gac | 240 |
| Val | Asn | Ala | Ala | Asp | Ala | Ala | Ala | Leu | Glu | His | Asp | Lys | Ala | Tyr | Asp |     |
| 65  |     |     |     | 70  |     |     |     | 75  |     |     |     | 80  |     |     |     |     |
| cag | cag | ctc | aaa | gcg | ggt | gac | aat | ccg | tac | ctg | cgg | tat | aac | cac | gcc | 288 |
| Gln | Gln | Leu | Lys | Ala | Gly | Asp | Asn | Pro | Tyr | Leu | Arg | Tyr | Asn | His | Ala |     |
|     |     |     |     | 85  |     |     |     | 90  |     |     |     | 95  |     |     |     |     |
| gac | gcc | gag | ttt | cag | gag | cgt | ctg | caa | gaa | gat | acg | tct | ttt | ggg | ggc | 336 |
| Asp | Ala | Glu | Phe | Gln | Glu | Arg | Leu | Gln | Glu | Asp | Thr | Ser | Phe | Gly | Gly |     |
|     |     |     | 100 |     |     |     | 105 |     |     |     | 110 |     |     |     |     |     |
| aac | ctc | ggg | cga | gca | gtc | ttc | cag | gcc | aag | aag | cgg | gtt | ctc | gaa | cct | 384 |
| Asn | Leu | Gly | Arg | Ala | Val | Phe | Gln | Ala | Lys | Lys | Arg | Val | Leu | Glu | Pro |     |
|     |     | 115 |     |     |     | 120 |     |     |     | 125 |     |     |     |     |     |     |
| ctc | ggt | ctg | gtt | gag | gaa | ggc | gct | aag | acg | gct | cct | gga | aag | aaa | cgt | 432 |
| Leu | Gly | Leu | Val | Glu | Glu | Gly | Ala | Lys | Thr | Ala | Pro | Gly | Lys | Lys | Arg |     |
|     | 130 |     |     |     | 135 |     |     |     | 140 |     |     |     |     |     |     |     |
| ccg | gta | gag | cag | tcg | cca | caa | gag | cca | gac | tcc | tcc | tcg | ggc | atc | ggc | 480 |
| Pro | Val | Glu | Gln | Ser | Pro | Gln | Glu | Pro | Asp | Ser | Ser | Ser | Gly | Ile | Gly |     |
| 145 |     |     |     | 150 |     |     |     | 155 |     |     |     | 160 |     |     |     |     |
| aag | aca | ggc | cag | cag | ccc | gct | aaa | aag | aga | ctc | aat | ttt | ggt | cag | act | 528 |
| Lys | Thr | Gly | Gln | Gln | Pro | Ala | Lys | Lys | Arg | Leu | Asn | Phe | Gly | Gln | Thr |     |
|     |     |     | 165 |     |     |     | 170 |     |     |     | 175 |     |     |     |     |     |
| ggc | gac | tca | gag | tca | gtc | ccc | gat | cca | caa | cct | ctc | gga | gaa | cct | cca | 576 |
| Gly | Asp | Ser | Glu | Ser | Val | Pro | Asp | Pro | Gln | Pro | Leu | Gly | Glu | Pro | Pro |     |
|     |     | 180 |     |     |     | 185 |     |     |     | 190 |     |     |     |     |     |     |
| gca | acc | ccc | gct | gct | gtg | gga | cct | act | aca | atg | gct | tca | ggc | ggt | ggc | 624 |
| Ala | Thr | Pro | Ala | Ala | Val | Gly | Pro | Thr | Thr | Met | Ala | Ser | Gly | Gly | Gly |     |
|     | 195 |     |     |     | 200 |     |     |     | 205 |     |     |     |     |     |     |     |
| gca | cca | atg | gca | gac | aat | aac | gaa | ggc | gcc | gac | gga | gtg | ggt | aat | gcc | 672 |
| Ala | Pro | Met | Ala | Asp | Asn | Asn | Glu | Gly | Ala | Asp | Gly | Val | Gly | Asn | Ala |     |
| 210 |     |     |     | 215 |     |     |     | 220 |     |     |     |     |     |     |     |     |
| tca | gga | aat | tgg | cat | tgc | gat | tcc | aca | tgg | ctg | ggc | gac | aga | gtc | atc | 720 |
| Ser | Gly | Asn | Trp | His | Cys | Asp | Ser | Thr | Trp | Leu | Gly | Asp | Arg | Val | Ile |     |
| 225 |     |     |     | 230 |     |     |     | 235 |     |     |     | 240 |     |     |     |     |
| acc | acc | agc | acc | cgc | acc | tgg | gcc | ttg | ccc | acc | tac | aat | aac | cac | ctc | 768 |
| Thr | Thr | Ser | Thr | Arg | Thr | Trp | Ala | Leu | Pro | Thr | Tyr | Asn | Asn | His | Leu |     |
|     |     |     | 245 |     |     |     | 250 |     |     |     | 255 |     |     |     |     |     |
| tac | aag | caa | atc | tcc | agt | gct | tca | acg | ggg | gcc | agc | aac | gac | aac | cac | 816 |
| Tyr | Lys | Gln | Ile | Ser | Ser | Ala | Ser | Thr | Gly | Ala | Ser | Asn | Asp | Asn | His |     |
|     |     |     | 260 |     |     |     | 265 |     |     |     | 270 |     |     |     |     |     |
| tac | ttc | ggc | tac | agc | acc | ccc | tgg | ggg | tat | ttt | gat | ttc | aac | aga | ttc | 864 |
| Tyr | Phe | Gly | Tyr | Ser | Thr | Pro | Trp | Gly | Tyr | Phe | Asp | Phe | Asn | Arg | Phe |     |
|     |     | 275 |     |     |     | 280 |     |     |     | 285 |     |     |     |     |     |     |
| cac | tgc | cac | ttt | tca | cca | cgt | gac | tgg | cag | cga | ctc | atc | aac | aac | aat | 912 |
| His | Cys | His | Phe | Ser | Pro | Arg | Asp | Trp | Gln | Arg | Leu | Ile | Asn | Asn | Asn |     |
|     | 290 |     |     |     | 295 |     |     |     | 300 |     |     |     |     |     |     |     |
| tgg | gga | ttc | cgg | ccc | aag | aga | ctc | aac | ttc | aaa | ctc | ttc | aac | atc | caa | 960 |
| Trp | Gly | Phe | Arg | Pro | Lys | Arg | Leu | Asn | Phe | Lys | Leu | Phe | Asn | Ile | Gln |     |
| 305 |     |     |     | 310 |     |     |     | 315 |     |     |     | 320 |     |     |     |     |
| gtc | aag | gag | gtc | acg | acg | aat | gat | ggc | gtc | aca | acc | atc | gct | aat | aac | 1008 |
| Val | Lys | Glu | Val | Thr | Thr | Asn | Asp | Gly | Val | Thr | Thr | Ile | Ala | Asn | Asn |     |
|     |     |     | 325 |     |     |     | 330 |     |     |     | 335 |     |     |     |     |     |
| ctt | acc | agc | acg | gtt | caa | gtc | ttc | tcg | gac | tcg | gag | tac | cag | ctt | ccg | 1056 |
| Leu | Thr | Ser | Thr | Val | Gln | Val | Phe | Ser | Asp | Ser | Glu | Tyr | Gln | Leu | Pro |     |
|     |     |     | 340 |     |     |     | 345 |     |     |     | 350 |     |     |     |     |     |
| tac | gtc | ctc | ggc | tct | gcg | cac | cag | ggc | tgc | ctc | cct | ccg | ttc | ccg | gcg | 1104 |
| Tyr | Val | Leu | Gly | Ser | Ala | His | Gln | Gly | Cys | Leu | Pro | Pro | Phe | Pro | Ala |     |
|     |     | 355 |     |     |     | 360 |     |     |     | 365 |     |     |     |     |     |     |
| gac | gtg | ttc | atg | att | ccg | caa | tac | ggc | tac | ctg | acg | ctc | aac | aat | ggc | 1152 |

```
Asp Val Phe Met Ile Pro Gln Tyr Gly Tyr Leu Thr Leu Asn Asn Gly
    370                 375                 380 agc caa gcc gtg gga cgt tca tcc ttt tac tgc ctg gaa tat ttc cct    1200
Ser Gln Ala Val Gly Arg Ser Ser Phe Tyr Cys Leu Glu Tyr Phe Pro
385                 390                 395                 400 tct cag atg ctg aga acg ggc aac aac ttt acc ttc agc tac acc ttt    1248
Ser Gln Met Leu Arg Thr Gly Asn Asn Phe Thr Phe Ser Tyr Thr Phe
            405                 410                 415 gag gaa gtg cct ttc cac agc agc tac gcg cac agc cag agc ctg gac    1296
Glu Glu Val Pro Phe His Ser Ser Tyr Ala His Ser Gln Ser Leu Asp
        420                 425                 430 cgg ctg atg aat cct ctc atc gac caa tac ctg tat ttc ctg aac aga    1344
Arg Leu Met Asn Pro Leu Ile Asp Gln Tyr Leu Tyr Phe Leu Asn Arg
    435                 440                 445 act caa aat cag tcc gga agt gcc caa aac aag gac ttg ctg ttt agc    1392
Thr Gln Asn Gln Ser Gly Ser Ala Gln Asn Lys Asp Leu Leu Phe Ser
450                 455                 460 cgt ggg tct cca gct ggc atg tct gtt cag ccc aaa aac tgg cta cct    1440
Arg Gly Ser Pro Ala Gly Met Ser Val Gln Pro Lys Asn Trp Leu Pro
465                 470                 475                 480 gga ccc tgt tat cgg cag cag cgc gtt tct aaa aca aaa aca gac aac    1488
Gly Pro Cys Tyr Arg Gln Gln Arg Val Ser Lys Thr Lys Thr Asp Asn
            485                 490                 495 aac aac agc aat ttt acc tgg act ggt gct tca aaa tat aac ctc aat    1536
Asn Asn Ser Asn Phe Thr Trp Thr Gly Ala Ser Lys Tyr Asn Leu Asn
        500                 505                 510 ggg cgt gaa tcc atc atc aac cct ggc act gct atg gcc tca cac aaa    1584
Gly Arg Glu Ser Ile Ile Asn Pro Gly Thr Ala Met Ala Ser His Lys
    515                 520                 525 gac gac gaa gac aag ttc ttt ccc atg agc ggt gtc atg att ttt gga    1632
Asp Asp Glu Asp Lys Phe Phe Pro Met Ser Gly Val Met Ile Phe Gly
530                 535                 540 aaa gag agc gcc gga gct tca aac act gca ttg gac aat gtc atg att    1680
Lys Glu Ser Ala Gly Ala Ser Asn Thr Ala Leu Asp Asn Val Met Ile
545                 550                 555                 560 aca gac gaa gag gaa att aaa gcc act aac cct gtg gcc acc gaa aga    1728
Thr Asp Glu Glu Glu Ile Lys Ala Thr Asn Pro Val Ala Thr Glu Arg
            565                 570                 575 ttt ggg acc gtg gca gtc aat ttc cag agc agc agc aca gac cct gcg    1776
Phe Gly Thr Val Ala Val Asn Phe Gln Ser Ser Ser Thr Asp Pro Ala
        580                 585                 590 acc gga gat gtg cat gct atg gga gca tta cct ggc atg gtg tgg caa    1824
Thr Gly Asp Val His Ala Met Gly Ala Leu Pro Gly Met Val Trp Gln
    595                 600                 605 gat aga gac gtg tac ctg cag ggt ccc att tgg gcc aaa att cct cac    1872
Asp Arg Asp Val Tyr Leu Gln Gly Pro Ile Trp Ala Lys Ile Pro His
610                 615                 620 aca gat gga cac ttt cac ccg tct cct ctt atg ggc ggc ttt gga ctc    1920
Thr Asp Gly His Phe His Pro Ser Pro Leu Met Gly Gly Phe Gly Leu
625                 630                 635                 640 aag aac ccg cct cct cag atc ctc atc aaa aac acg cct gtt cct gcg    1968
Lys Asn Pro Pro Pro Gln Ile Leu Ile Lys Asn Thr Pro Val Pro Ala
            645                 650                 655 aat cct ccg gcg gag ttt tca gct aca aag ttt gct tca ttc atc acc    2016
Asn Pro Pro Ala Glu Phe Ser Ala Thr Lys Phe Ala Ser Phe Ile Thr
        660                 665                 670 caa tac tcc aca gga caa gtg agt gtg gaa att gaa tgg gag ctg cag    2064
Gln Tyr Ser Thr Gly Gln Val Ser Val Glu Ile Glu Trp Glu Leu Gln
    675                 680                 685
```

| | | | | | | | | | | | | | | | | |
|---|---|---|---|---|---|---|---|---|---|---|---|---|---|---|---|---|
| aaa | gaa | aac | agc | aag | cgc | tgg | aat | ccc | gaa | gtg | cag | tac | aca | tcc | aat | 2112 |
| Lys | Glu | Asn | Ser | Lys | Arg | Trp | Asn | Pro | Glu | Val | Gln | Tyr | Thr | Ser | Asn | |
| | | | 690 | | | | 695 | | | | 700 | | | | | |
| tat | gca | aaa | tct | gcc | aac | gtt | gat | ttt | act | gtg | gac | aac | aat | gga | ctt | 2160 |
| Tyr | Ala | Lys | Ser | Ala | Asn | Val | Asp | Phe | Thr | Val | Asp | Asn | Asn | Gly | Leu | |
| 705 | | | | | 710 | | | | | 715 | | | | | 720 | |
| tat | act | gag | cct | cgc | ccc | att | ggc | acc | cgt | tac | ctt | acc | cgt | ccc | ctg | 2208 |
| Tyr | Thr | Glu | Pro | Arg | Pro | Ile | Gly | Thr | Arg | Tyr | Leu | Thr | Arg | Pro | Leu | |
| | | | | 725 | | | | | 730 | | | | | 735 | | |

<210> SEQ ID NO 8
<211> LENGTH: 736
<212> TYPE: PRT
<213> ORGANISM: Artificial Sequence
<220> FEATURE:
<223> OTHER INFORMATION: Synthetic Construct

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

-continued

```
Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Phe Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
```

<210> SEQ ID NO 9
<211> LENGTH: 2205
<212> TYPE: DNA
<213> ORGANISM: Artificial Sequence
<220> FEATURE:
<223> OTHER INFORMATION: AAV2-yfVP1
<220> FEATURE:
<221> NAME/KEY: CDS
<222> LOCATION: (1)..(2205)
<223> OTHER INFORMATION: AAV2-yfVP1

<400> SEQUENCE: 9

```
atg gct gcc gat ggt tat ctt cca gat tgg ctc gag gac act ctc tct     48
Met Ala Ala Asp Gly Tyr Leu Pro Asp Trp Leu Glu Asp Thr Leu Ser
 1               5                  10                  15 gaa gga ata aga cag tgg tgg aag ctc aaa cct ggc cca cca cca cca     96
Glu Gly Ile Arg Gln Trp Trp Lys Leu Lys Pro Gly Pro Pro Pro Pro
            20                  25                  30 aag ccc gca gag cgg cat aag gac gac agc agg ggt ctt gtg ctt cct    144
Lys Pro Ala Glu Arg His Lys Asp Asp Ser Arg Gly Leu Val Leu Pro
        35                  40                  45 ggg tac aag tac ctc gga ccc ttc aac gga ctc gac aag gga gag ccg    192
Gly Tyr Lys Tyr Leu Gly Pro Phe Asn Gly Leu Asp Lys Gly Glu Pro
     50                  55                  60 gtc aac gag gca gac gcc gcg gcc ctc gag cac gac aaa gcc tac gac    240
Val Asn Glu Ala Asp Ala Ala Ala Leu Glu His Asp Lys Ala Tyr Asp
 65                  70                  75                  80 cgg cag ctc gac agc gga gac aac ccg tac ctc aag tac aac cac gcc    288
Arg Gln Leu Asp Ser Gly Asp Asn Pro Tyr Leu Lys Tyr Asn His Ala
                 85                  90                  95 gac gcg gag ttt cag gag cgc ctt aaa gaa gat acg tct ttt ggg ggc    336
Asp Ala Glu Phe Gln Glu Arg Leu Lys Glu Asp Thr Ser Phe Gly Gly
            100                 105                 110 aac ctc gga cga gca gtc ttc cag gcg aaa aag agg gtt ctt gaa cct    384
Asn Leu Gly Arg Ala Val Phe Gln Ala Lys Lys Arg Val Leu Glu Pro
        115                 120                 125 ctg ggc ctg gtt gag gaa cct gtt aag acg gct ccg gga aaa aag agg    432
Leu Gly Leu Val Glu Glu Pro Val Lys Thr Ala Pro Gly Lys Lys Arg
    130                 135                 140 ccg gta gag cac tct cct gtg gag cca gac tcc tcc tcg gga acc gga    480
Pro Val Glu His Ser Pro Val Glu Pro Asp Ser Ser Ser Gly Thr Gly
145                 150                 155                 160 aag gcg ggc cag cag cct gca aga aaa aga ttg aat ttt ggt cag act    528
Lys Ala Gly Gln Gln Pro Ala Arg Lys Arg Leu Asn Phe Gly Gln Thr
                165                 170                 175 gga gac gca gac tca gta cct gac ccc cag cct ctc gga cag cca cca    576
Gly Asp Ala Asp Ser Val Pro Asp Pro Gln Pro Leu Gly Gln Pro Pro
            180                 185                 190 gca gcc ccc tct ggt ctg gga act aat acg atg gct aca ggc agt ggc    624
Ala Ala Pro Ser Gly Leu Gly Thr Asn Thr Met Ala Thr Gly Ser Gly
        195                 200                 205 gca cca atg gca gac aat aac gag ggc gcc gac gga gtg ggt aat tcc    672
Ala Pro Met Ala Asp Asn Asn Glu Gly Ala Asp Gly Val Gly Asn Ser
    210                 215                 220 tcg gga aat tgg cat tgc gat tcc aca tgg atg ggc gac aga gtc atc    720
Ser Gly Asn Trp His Cys Asp Ser Thr Trp Met Gly Asp Arg Val Ile
225                 230                 235                 240 acc acc agc acc cga acc tgg gcc ctg ccc acc tac aac aac cac ctc    768
Thr Thr Ser Thr Arg Thr Trp Ala Leu Pro Thr Tyr Asn Asn His Leu
                245                 250                 255
```

-continued

| | | |
|---|---|---|
| tac aaa caa att tcc agc caa tca gga gcc tcg aac gac aat cac tac<br>Tyr Lys Gln Ile Ser Ser Gln Ser Gly Ala Ser Asn Asp Asn His Tyr<br>260 265 270 | | 816 |
| ttt ggc tac agc acc cct tgg ggg tat ttt gac ttc aac aga ttc cac<br>Phe Gly Tyr Ser Thr Pro Trp Gly Tyr Phe Asp Phe Asn Arg Phe His<br>275 280 285 | | 864 |
| tgc cac ttt tca cca cgt gac tgg caa aga ctc atc aac aac aac tgg<br>Cys His Phe Ser Pro Arg Asp Trp Gln Arg Leu Ile Asn Asn Asn Trp<br>290 295 300 | | 912 |
| gga ttc cga ccc aag aga ctc aac ttc aag ctc ttt aac att caa gtc<br>Gly Phe Arg Pro Lys Arg Leu Asn Phe Lys Leu Phe Asn Ile Gln Val<br>305 310 315 320 | | 960 |
| aaa gag gtc acg cag aat gac ggt acg acg acg att gcc aat aac ctt<br>Lys Glu Val Thr Gln Asn Asp Gly Thr Thr Thr Ile Ala Asn Asn Leu<br>325 330 335 | | 1008 |
| acc agc acg gtt cag gtg ttt act gac tcg gag tac cag ctc ccg tac<br>Thr Ser Thr Val Gln Val Phe Thr Asp Ser Glu Tyr Gln Leu Pro Tyr<br>340 345 350 | | 1056 |
| gtc ctc ggc tcg gcg cat caa gga tgc ctc ccg ccg ttc cca gca gac<br>Val Leu Gly Ser Ala His Gln Gly Cys Leu Pro Pro Phe Pro Ala Asp<br>355 360 365 | | 1104 |
| gtc ttc atg gtg cca cag tat gga tac ctc acc ctg aac aac ggg agt<br>Val Phe Met Val Pro Gln Tyr Gly Tyr Leu Thr Leu Asn Asn Gly Ser<br>370 375 380 | | 1152 |
| cag gca gta gga cgc tct tca ttt tac tgc ctg gag tac ttt cct tct<br>Gln Ala Val Gly Arg Ser Ser Phe Tyr Cys Leu Glu Tyr Phe Pro Ser<br>385 390 395 400 | | 1200 |
| cag atg ctg cgt acc gga aac aac ttt acc ttc agc tac act ttt gag<br>Gln Met Leu Arg Thr Gly Asn Asn Phe Thr Phe Ser Tyr Thr Phe Glu<br>405 410 415 | | 1248 |
| gac gtt cct ttc cac agc agc tac gct cac agc cag agt ctg gac cgt<br>Asp Val Pro Phe His Ser Ser Tyr Ala His Ser Gln Ser Leu Asp Arg<br>420 425 430 | | 1296 |
| ctc atg aat cct ctc atc gac cag tac ctg tat ttc ttg agc aga aca<br>Leu Met Asn Pro Leu Ile Asp Gln Tyr Leu Tyr Phe Leu Ser Arg Thr<br>435 440 445 | | 1344 |
| aac act cca agt gga acc acc acg cag tca agg ctt cag ttt tct cag<br>Asn Thr Pro Ser Gly Thr Thr Thr Gln Ser Arg Leu Gln Phe Ser Gln<br>450 455 460 | | 1392 |
| gcc gga gcg agt gac att cgg gac cag tct agg aac tgg ctt cct gga<br>Ala Gly Ala Ser Asp Ile Arg Asp Gln Ser Arg Asn Trp Leu Pro Gly<br>465 470 475 480 | | 1440 |
| ccc tgt tac cgc cag cag cga gta tca aag aca tct gcg gat aac aac<br>Pro Cys Tyr Arg Gln Gln Arg Val Ser Lys Thr Ser Ala Asp Asn Asn<br>485 490 495 | | 1488 |
| aac agt gaa tac tcg tgg act gga gct acc aag tac cac ctc aat ggc<br>Asn Ser Glu Tyr Ser Trp Thr Gly Ala Thr Lys Tyr His Leu Asn Gly<br>500 505 510 | | 1536 |
| aga gac tct ctg gtg aat ccg ggc ccg gcc atg gca agc cac aag gac<br>Arg Asp Ser Leu Val Asn Pro Gly Pro Ala Met Ala Ser His Lys Asp<br>515 520 525 | | 1584 |
| gat gaa gaa aag ttt ttt cct cag agc ggg gtt ctc atc ttt ggg aag<br>Asp Glu Glu Lys Phe Phe Pro Gln Ser Gly Val Leu Ile Phe Gly Lys<br>530 535 540 | | 1632 |
| caa ggc tca gag aaa aca aat gtg gac att gaa aag gtc atg att aca<br>Gln Gly Ser Glu Lys Thr Asn Val Asp Ile Glu Lys Val Met Ile Thr<br>545 550 555 560 | | 1680 |
| gac gaa gag gaa atc agg aca acc aat ccc gtg gct acg gag cag tat<br>Asp Glu Glu Glu Ile Arg Thr Thr Asn Pro Val Ala Thr Glu Gln Tyr | | 1728 |

```
                          565                 570                 575
ggt tct gta tct acc aac ctc cag aga ggc aac aga caa gca gct acc     1776
Gly Ser Val Ser Thr Asn Leu Gln Arg Gly Asn Arg Gln Ala Ala Thr
        580                 585                 590 gca gat gtc aac aca caa ggc gtt ctt cca ggc atg gtc tgg cag gac     1824
Ala Asp Val Asn Thr Gln Gly Val Leu Pro Gly Met Val Trp Gln Asp
            595                 600                 605 aga gat gtg tac ctt cag ggg ccc atc tgg gca aag att cca cac acg     1872
Arg Asp Val Tyr Leu Gln Gly Pro Ile Trp Ala Lys Ile Pro His Thr
    610                 615                 620 gac gga cat ttt cac ccc tct ccc ctc atg ggt gga ttc gga ctt aaa     1920
Asp Gly His Phe His Pro Ser Pro Leu Met Gly Gly Phe Gly Leu Lys
625                 630                 635                 640 cac cct cct cca cag att ctc atc aag aac acc ccg gta cct gcg aat     1968
His Pro Pro Pro Gln Ile Leu Ile Lys Asn Thr Pro Val Pro Ala Asn
                645                 650                 655 cct tcg acc acc ttc agt gcg gca aag ttt gct tcc ttc atc aca cag     2016
Pro Ser Thr Thr Phe Ser Ala Ala Lys Phe Ala Ser Phe Ile Thr Gln
            660                 665                 670 tac tcc acg gga cag gtc agc gtg gag atc gag tgg gag ctg cag aag     2064
Tyr Ser Thr Gly Gln Val Ser Val Glu Ile Glu Trp Glu Leu Gln Lys
        675                 680                 685 gaa aac agc aaa cgc tgg aat ccc gaa att cag tac act tcc aac tac     2112
Glu Asn Ser Lys Arg Trp Asn Pro Glu Ile Gln Tyr Thr Ser Asn Tyr
    690                 695                 700 aac aag tct gtt aat gtg gac ttt act gtg gac act aat ggc gtg tat     2160
Asn Lys Ser Val Asn Val Asp Phe Thr Val Asp Thr Asn Gly Val Tyr
705                 710                 715                 720 tca gag cct cgc ccc att ggc acc aga tac ctg act cgt aat ctg         2205
Ser Glu Pro Arg Pro Ile Gly Thr Arg Tyr Leu Thr Arg Asn Leu
                725                 730                 735

<210> SEQ ID NO 10
<211> LENGTH: 735
<212> TYPE: PRT
<213> ORGANISM: Artificial Sequence
<220> FEATURE:
<223> OTHER INFORMATION: Synthetic Construct

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140
```

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Phe Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
```

```
                    565                 570                 575
Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 11
<211> LENGTH: 2208
<212> TYPE: DNA
<213> ORGANISM: Artificial Sequence
<220> FEATURE:
<223> OTHER INFORMATION: AAV9-yfVP1
<220> FEATURE:
<221> NAME/KEY: CDS
<222> LOCATION: (1)..(2208)
<223> OTHER INFORMATION: AAV9-yfVP1

<400> SEQUENCE: 11 atg gct gcc gat ggt tat ctt cca gat tgg ctc gag gac aac ctt agt      48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc     336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct     384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg     432
```

-continued

```
                Leu Gly Leu Val Glu Glu Ala Ala Lys Thr Ala Pro Gly Lys Lys Arg
                    130                 135                 140 cct gta gag cag tct cct cag gaa ccg gac tcc tcc gcg ggt att ggc        480
Pro Val Glu Gln Ser Pro Gln Glu Pro Asp Ser Ser Ala Gly Ile Gly
145                 150                 155                 160 aaa tcg ggt gca cag ccc gct aaa aag aga ctc aat ttc ggt cag act        528
Lys Ser Gly Ala Gln Pro Ala Lys Lys Arg Leu Asn Phe Gly Gln Thr
                165                 170                 175 ggc gac aca gag tca gtc cca gac cct caa cca atc gga gaa cct ccc        576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc        624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc        672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc        720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc        768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac        816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga        864
Ala Tyr Phe Gly Tyr Ser Thr Pro Trp Gly Tyr Phe Asp Phe Asn Arg
        275                 280                 285 ttc cac tgc cac ttc tca cca cgt gac tgg cag cga ctc atc aac aac        912
Phe His Cys His Phe Ser Pro Arg Asp Trp Gln Arg Leu Ile Asn Asn
    290                 295                 300 aac tgg gga ttc cgg cct aag cga ctc aac ttc aag ctc ttc aac att        960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gcc aat        1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc        1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca        1104
Pro Tyr Val Leu Gly Ser Ala His Glu Gly Cys Leu Pro Pro Phe Pro
        355                 360                 365 gcg gac gtt ttc atg att cct cag tac ggg tat ctg acg ctt aat gat        1152
Ala Asp Val Phe Met Ile Pro Gln Tyr Gly Tyr Leu Thr Leu Asn Asp
    370                 375                 380 gga agc cag gcc gtg ggt cgt tcg tcc ttt tac tgc ctg gaa tat ttc        1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag        1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg        1296
Phe Glu Asn Val Pro Phe His Ser Ser Tyr Ala His Ser Gln Ser Leu
            420                 425                 430 gac cga cta atg aat cca ctc atc gac caa tac ttg tac ttt ctc tca        1344
Asp Arg Leu Met Asn Pro Leu Ile Asp Gln Tyr Leu Tyr Phe Leu Ser
        435                 440                 445
```

| | |
|---|---|
| aag act att aac ggt tct gga cag aat caa caa acg cta aaa ttc agt<br>Lys Thr Ile Asn Gly Ser Gly Gln Asn Gln Gln Thr Leu Lys Phe Ser<br>450                             455                         460 | 1392 |
| gtg gcc gga ccc agc aac atg gct gtc cag gga aga aac tac ata cct<br>Val Ala Gly Pro Ser Asn Met Ala Val Gln Gly Arg Asn Tyr Ile Pro<br>465                       470                     475                 480 | 1440 |
| gga ccc agc tac cga caa caa cgt gtc tca acc act gtg act caa aac<br>Gly Pro Ser Tyr Arg Gln Gln Arg Val Ser Thr Thr Val Thr Gln Asn<br>                   485                   490                   495 | 1488 |
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>500                           505                         510 | 1536 |
| gga cgt aat agc ttg atg aat cct gga cct gct atg gcc agc cac aaa<br>Gly Arg Asn Ser Leu Met Asn Pro Gly Pro Ala Met Ala Ser His Lys<br>         515                   520                   525 | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>530                           535                       540 | 1632 |
| aaa caa gga act gga aga gac aac gtg gat gcg gac aaa gtc atg ata<br>Lys Gln Gly Thr Gly Arg Asp Asn Val Asp Ala Asp Lys Val Met Ile<br>545                         550                     555                 560 | 1680 |
| acc aac gaa gaa gaa att aaa act act aac ccg gta gca acg gag tcc<br>Thr Asn Glu Glu Glu Ile Lys Thr Thr Asn Pro Val Ala Thr Glu Ser<br>                   565                   570                   575 | 1728 |
| tat gga caa gtg gcc aca aac cac cag agt gcc caa gca cag gcg cag<br>Tyr Gly Gln Val Ala Thr Asn His Gln Ser Ala Gln Ala Gln Ala Gln<br>                   580                   585                   590 | 1776 |
| acc ggc tgg gtt caa aac caa gga ata ctt ccg ggt atg gtt tgg cag<br>Thr Gly Trp Val Gln Asn Gln Gly Ile Leu Pro Gly Met Val Trp Gln<br>         595                   600                   605 | 1824 |
| gac aga gat gtg tac ctg caa gga ccc att tgg gcc aaa att cct cac<br>Asp Arg Asp Val Tyr Leu Gln Gly Pro Ile Trp Ala Lys Ile Pro His<br>610                         615                     620 | 1872 |
| acg gac ggc aac ttt cac cct tct ccg ctg atg gga ggg ttt gga atg<br>Thr Asp Gly Asn Phe His Pro Ser Pro Leu Met Gly Gly Phe Gly Met<br>625                       630                     635                 640 | 1920 |
| aag cac ccg cct cct cag atc ctc atc aaa aac aca cct gta cct gcg<br>Lys His Pro Pro Pro Gln Ile Leu Ile Lys Asn Thr Pro Val Pro Ala<br>                   645                   650                   655 | 1968 |
| gat cct cca acg gcc ttc aac aag gac aag ctg aac tct ttc atc acc<br>Asp Pro Pro Thr Ala Phe Asn Lys Asp Lys Leu Asn Ser Phe Ile Thr<br>                   660                   665                   670 | 2016 |
| cag tat tct act ggc caa gtc agc gtg gag atc gag tgg gag ctg cag<br>Gln Tyr Ser Thr Gly Gln Val Ser Val Glu Ile Glu Trp Glu Leu Gln<br>         675                   680                   685 | 2064 |
| aag gaa aac agc aag cgc tgg aac ccg gag atc cag tac act tcc aac<br>Lys Glu Asn Ser Lys Arg Trp Asn Pro Glu Ile Gln Tyr Thr Ser Asn<br>690                         695                     700 | 2112 |
| tat tac aag tct aat aat gtt gaa ttt gct gtt aat act gaa ggt gta<br>Tyr Tyr Lys Ser Asn Asn Val Glu Phe Ala Val Asn Thr Glu Gly Val<br>705                         710                     715                 720 | 2160 |
| tat agt gaa ccc cgc ccc att ggc acc aga tac ctg act cgt aat ctg<br>Tyr Ser Glu Pro Arg Pro Ile Gly Thr Arg Tyr Leu Thr Arg Asn Leu<br>                   725                   730                   735 | 2208 |

<210> SEQ ID NO 12
<211> LENGTH: 736
<212> TYPE: PRT
<213> ORGANISM: Artificial Sequence
<220> FEATURE:
<223> OTHER INFORMATION: Synthetic Construct -continued

<400> SEQUENCE: 12

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
```

```
                    405                 410                 415
Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Phe Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
                625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 125
<212> TYPE: DNA
<213> ORGANISM: adeno-associated virus 3
<220> FEATURE:
<221> NAME/KEY: misc_feature
<222> LOCATION: (1)..(125)
<223> OTHER INFORMATION: Inverted Terminal Repeat

<400> SEQUENCE: 13
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaa                                                                 125
```

<210> SEQ ID NO 14
<211> LENGTH: 125
<212> TYPE: DNA
<213> ORGANISM: adeno-associated virus 3
<220> FEATURE:
<221> NAME/KEY: misc_feature
<222> LOCATION: (1)..(125)
<223> OTHER INFORMATION: Inverted Terminal Repeat

<400> SEQUENCE: 14

```
ttggccactc cctctatgcg cactcgctcg ctcggtgggg cctggcgacc aaaggtcgcc       60
agacggacgt gctttgcacg tccggcccca ccgagcgagc gagtgcgcat agagggagtg      120
gccaa                                                                  125
```

<210> SEQ ID NO 15
<211> LENGTH: 1611
<212> TYPE: DNA
<213> ORGANISM: adeno-associated virus 2
<220> FEATURE:
<221> NAME/KEY: CDS
<222> LOCATION: (1)..(1611)
<223> OTHER INFORMATION: AAV2 Rep protein

<400> SEQUENCE: 15

```
atg ccg ggg ttt tac gag att gtg att aag gtc ccc agc gac ctt gac        48
Met Pro Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag        96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att       144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttt ctg       192
Glu Gln Ala Pro Leu Thr Val Ala Glu Lys Leu Gln Arg Asp Phe Leu
    50                  55                  60 acg gaa tgg cgc cgt gtg agt aag gcc ccg gag gcc ctt ttc ttt gtg       240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa       288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att       336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg       384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg       432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa       480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta       528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat       576
Ser Ala Cys Leu Asn Leu Thr Glu Arg Lys Arg Leu Val Ala Gln His
            180                 185                 190
```

```
ctg acg cac gtg tcg cag acg cag gag cag aac aaa gag aat cag aat    624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac    672
Pro Asn Ser Asp Ala Pro Val Ile Arg Ser Lys Thr Ser Ala Arg Tyr
210                 215                 220 atg gag ctg gtc ggg tgg ctc gtg gac aag ggg att acc tcg gag aag    720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc    768
Gln Trp Ile Gln Glu Asp Gln Ala Ser Tyr Ile Ser Phe Asn Ala Ala
            245                 250                 255 tcc aac tcg cgg tcc caa atc aag gct gcc ttg gac aat gcg gga aag    816
Ser Asn Ser Arg Ser Gln Ile Lys Ala Ala Leu Asp Asn Ala Gly Lys
        260                 265                 270 att atg agc ctg act aaa acc gcc ccc gac tac ctg gtg ggc cag cag    864
Ile Met Ser Leu Thr Lys Thr Ala Pro Asp Tyr Leu Val Gly Gln Gln
    275                 280                 285 ccc gtg gag gac att tcc agc aat cgg att tat aaa att ttg gaa cta    912
Pro Val Glu Asp Ile Ser Ser Asn Arg Ile Tyr Lys Ile Leu Glu Leu
290                 295                 300 aac ggg tac gat ccc caa tat gcg gct tcc gtc ttt ctg gga tgg gcc    960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca   1008
Thr Lys Lys Phe Gly Lys Arg Asn Thr Ile Trp Leu Phe Gly Pro Ala
            325                 330                 335 act acc ggg aag acc aac atc gcg gag gcc ata gcc cac act gtg ccc   1056
Thr Thr Gly Lys Thr Asn Ile Ala Glu Ala Ile Ala His Thr Val Pro
        340                 345                 350 ttc tac ggg tgc gta aac tgg acc aat gag aac ttt ccc ttc aac gac   1104
Phe Tyr Gly Cys Val Asn Trp Thr Asn Glu Asn Phe Pro Phe Asn Asp
    355                 360                 365 tgt gtc gac aag atg gtg atc tgg tgg gag gag ggg aag atg acc gcc   1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc   1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg   1248
Val Asp Gln Lys Cys Lys Ser Ser Ala Gln Ile Asp Pro Thr Pro Val
            405                 410                 415 atc gtc acc tcc aac acc aac atg tgc gcc gtg att gac ggg aac tca   1296
Ile Val Thr Ser Asn Thr Asn Met Cys Ala Val Ile Asp Gly Asn Ser
        420                 425                 430 acg acc ttc gaa cac cag cag ccg ttg caa gac cgg atg ttc aaa ttt   1344
Thr Thr Phe Glu His Gln Gln Pro Leu Gln Asp Arg Met Phe Lys Phe
    435                 440                 445 gaa ctc acc cgc cgt ctg gat cat gac ttt ggg aag gtc acc aag cag   1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg   1440
Glu Val Lys Asp Phe Phe Arg Trp Ala Lys Asp His Val Val Glu Val
465                 470                 475                 480 gag cat gaa ttc tac gtc aaa aag ggt gga gcc aag aaa aga ccc gcc   1488
Glu His Glu Phe Tyr Val Lys Lys Gly Gly Ala Lys Lys Arg Pro Ala
            485                 490                 495 ccc agt gac gca gat ata agt gag ccc aaa cgg gtg cgc gag tca gtt   1536
Pro Ser Asp Ala Asp Ile Ser Glu Pro Lys Arg Val Arg Glu Ser Val
        500                 505                 510
```

```
gcg cag cca tcg acg tca gac gcg gaa gct tcg atc aac tac gca gac       1584
Ala Gln Pro Ser Thr Ser Asp Ala Glu Ala Ser Ile Asn Tyr Ala Asp
        515                 520                 525 aga ttg gct cga gga cac tct ctc tga                                    1611
Arg Leu Ala Arg Gly His Ser Leu
        530             535

<210> SEQ ID NO 16
<211> LENGTH: 536
<212> TYPE: PRT
<213> ORGANISM: adeno-associated virus 2

<400> SEQUENCE: 16

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335
```

-continued

```
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
        515                 520                 525
Arg Leu Ala Arg Gly His Ser Leu
    530                 535

<210> SEQ ID NO 17
<211> LENGTH: 32
<212> TYPE: DNA
<213> ORGANISM: Artificial Sequence
<220> FEATURE:
<223> OTHER INFORMATION: Primer AAV1-F

<400> SEQUENCE: 17
cgaccaatac ctgtatttcc tgaacagaac tc                                  32

<210> SEQ ID NO 18
<211> LENGTH: 32
<212> TYPE: DNA
<213> ORGANISM: Artificial Sequence
<220> FEATURE:
<223> OTHER INFORMATION: Primer yfAAV1-R

<400> SEQUENCE: 18
gagttctgtt caggaaatac aggtattggt cg                                  32

<210> SEQ ID NO 19
<211> LENGTH: 34
<212> TYPE: DNA
<213> ORGANISM: Artificial Sequence
<220> FEATURE:
<223> OTHER INFORMATION: Primer yfAAV2-F

<400> SEQUENCE: 19
cgaccagtac ctgtatttct tgagcagaac aaac                                34

<210> SEQ ID NO 20
<211> LENGTH: 34
```

```
<212> TYPE: DNA
<213> ORGANISM: Artificial Sequence
<220> FEATURE:
<223> OTHER INFORMATION: Primer yfAAV2-R

<400> SEQUENCE: 20
gtttgttctg ctcaagaaat acaggtactg gtcg                                  34

<210> SEQ ID NO 21
<211> LENGTH: 30
<212> TYPE: DNA
<213> ORGANISM: Artificial Sequence
<220> FEATURE:
<223> OTHER INFORMATION: Primer yfAAV9-F

<400> SEQUENCE: 21
cgaccaatac ttgtactttc tctcaaagac                                       30

<210> SEQ ID NO 22
<211> LENGTH: 30
<212> TYPE: DNA
<213> ORGANISM: Artificial Sequence
<220> FEATURE:
<223> OTHER INFORMATION: Primer yfAAV9-R

<400> SEQUENCE: 22
gtctttgaga gaaagtacaa gtattggtcg                                       30

<210> SEQ ID NO 23
<211> LENGTH: 1120
<212> TYPE: DNA
<213> ORGANISM: Homo sapiens
<220> FEATURE:
<221> NAME/KEY: misc_feature
<222> LOCATION: (1)..(1120)
<223> OTHER INFORMATION: SynI promoter

<400> SEQUENCE: 23
ttaattaagg gttttggcta cgtccagagc agaggaatga gggcatgtag actaaatatg      60
ttcgtgtgga agaggctgaa tacacatcag agttactgct gcaggaaatg cttctgcatt     120
gcatacccag agtttccttg ctcatctgag agcatgtgtt ttttccagat gtgtgtactt     180
gtgtgagatt ctctgggtgt gtgtcaatgt gttgcctgaa cgtgcattgc tcaatatgct     240
catgtgtgtt accctgggct tgtacatcta catatatacc tggatgcccg tgtgttctgt     300
gatgtacata taccctgtgt cattccttgt ttttctattt gtgttattcc atgtgttcct     360
tcaggctctc actacccaag tgtccacctc cgcctgtctg gtgatgttta cgctaccccg     420
tgctcttttc tttgcctgac agtgttgtcg tggaagacat ctcgccagga acactgcagt     480
aaggagaatt tctagtttta tgttcccctc cgagtatgct tctatcccga ccctcaaccc     540
caaaatgcct tcagaggtga aaatcaacac tggaaacaca agtatctggg aagggtaaca     600
atgcaagtta gcctgaggat ttaggaggag gctgaaaaac agagtaggag ccttactacg     660
ggtccagacc ctacggacaa gaacccccac tcccactccc caaattgcgc attccctccc     720
ccatcagagg gggagggggaa gaggatgcag cgcggcgcgg cgcgtgcgca ctgtcggatt     780
tagtaccgcg gacagagcct tcgccccccgc tgccggcgcg cgccaccacc tcccagcac     840 caaaggcggg ctgacgtcac tctccagcct tccccaaact cccctacctc accgccttgg     900
tcgcgtccgt gcagcggtga gtccagtcgg gccgcaccac aagaggtgca agatagggg      960 gtgcaggcgc gaccatacgc tctgcggcgg cagagcctca gcgctgcctc agtctgcagc    1020
```

```
gggcagcaga ggagtcgcgt cgtgccagag agcgccgccg tgctcctgag cccccttgcgc    1080 tccgcccccg cggcccaccg acccactgcc ccttggatcc                          1120
```

<210> SEQ ID NO 24
<211> LENGTH: 1311
<212> TYPE: DNA
<213> ORGANISM: Homo sapiens
<220> FEATURE:
<221> NAME/KEY: misc_feature
<222> LOCATION: (1)..(1311)
<223> OTHER INFORMATION: MBP promoter

<400> SEQUENCE: 24

```
agatctgcat gtttcactaa ttgtgtaata atgctctgct ctataaatat ccaaatgtaa      60
aagtctgcat tgggatttcg tttgactgaa ggcaatatta acgactaaac tgcactcgcc     120
cctaccaaaa acgctgcaca tccatagatt tagacttctt cgcatacttc ttatgtgttg     180
ggagaagcta ctttggggac aaaaatgccc ttctctgtgc ctcacaaata actgcattca     240
gggacacaaa gcccaactgt tgcaaaaata ttagtattca gatgttcttg tgttttgtta     300
atgcatttaa ttatgtacaa tatagctatt gttttccttt cacatttgca ttaatttata     360
ttagctagag aacataaagc acagctataa aatcagacta atcatttctg ttgttcttgc     420
aacctataaa taagcattgc atccctgcaa aaactgcagc tttgtactga ccacagtatt     480
cttcacgttg cttttttcaaa cactacagtg caatgatgta cttaataata tgttataaag    540
ctaattctaa atgccccact tctttcatgc atgaattgca aaaagatgtg gcaagttttg     600
tttctaccaa gaaaactaaa aacacctttt gtcaaataaa tgctccttgc atatttaact     660
tatgcaccag tggccttta aacagtcaat gtcccatcaa ggtgcctgca catctgggct      720
ctccgggagc agccatggca gcacccggga agaaacgctg atgtggctgc tctgcatgct     780
cagatgactt catcgggaag cctgggtgca ttttacgctg ggtgccaaat ctcgagtaac     840
tgaggaattc ccagagcctt ctgaaacaca gagctgcaat aaggctgctc catccaggtt     900
agctccatcc taggccaagg gctttatgag gactgcacat attctgtggg ttttataggaa    960 gacagctagg tcaagacccc tcagagaaag ctgctttgtc cggtgctcag ctttgcacag    1020
gcccgtattc atatctcatt gttgtttgca ggagaggcag atgcgaacca gaacaatggg    1080
acctcctctc aggacacagc ggtgactgac tccaagcgca cagcggaccc gaagaatgcc    1140
tggcaggatg cccacccagc tgacccaggg agccgccccc acttgatccg cctctttttcc   1200 cgagatgccc cggggaggga ggacaacacc ttcaaagaca ggccctctga gtccgacgag    1260
ctccagacca tccaagaaga cagtgcagcc acctccgaga gcctggatgt g             1311
```

<210> SEQ ID NO 25
<211> LENGTH: 23
<212> TYPE: DNA
<213> ORGANISM: Artificial Sequence
<220> FEATURE:
<223> OTHER INFORMATION: Primer GFP qPCR For

<400> SEQUENCE: 25

```
gaagcagcac gacttcttca aga                                              23
```

<210> SEQ ID NO 26
<211> LENGTH: 23
<212> TYPE: DNA
<213> ORGANISM: Artificial Sequence
<220> FEATURE:
<223> OTHER INFORMATION: Primer GFP qPCR Rev

```
<400> SEQUENCE: 26
ggatgttgcc atcctccttg aaa                                           23

<210> SEQ ID NO 27
<211> LENGTH: 19
<212> TYPE: DNA
<213> ORGANISM: Artificial Sequence
<220> FEATURE:
<223> OTHER INFORMATION: nucleotide sequence designed to nucleotide 831-
      851 of Mus musculus AADC (Genebank accession No. NM_016672)

<400> SEQUENCE: 27
tgcctttatg tcctgaatt                                                19

<210> SEQ ID NO 28
<211> LENGTH: 60
<212> TYPE: DNA
<213> ORGANISM: Artificial Sequence
<220> FEATURE:
<223> OTHER INFORMATION: miAADC producing sequence
<220> FEATURE:
<221> NAME/KEY: misc_feature
<222> LOCATION: (42)..(60)
<223> OTHER INFORMATION: Target sequence to AADC

<400> SEQUENCE: 28
gaattcagga cagataaagg cagttttggc cactgactga ctgcctttat gtcctgaatt   60

<210> SEQ ID NO 29
<211> LENGTH: 1104
<212> TYPE: DNA
<213> ORGANISM: Artificial Sequence
<220> FEATURE:
<223> OTHER INFORMATION: GFP-miRNA-AADC
<220> FEATURE:
<221> NAME/KEY: misc_feature
<222> LOCATION: (127)..(846)
<223> OTHER INFORMATION: GFP coding sequence
<220> FEATURE:
<221> NAME/KEY: misc_feature
<222> LOCATION: (932)..(991)
<223> OTHER INFORMATION: miRNA sequence for AADC

<400> SEQUENCE: 29
tctctggcta actagagaac ccactgctta ctggcttatc gaaattaata cgactcacta   60
tagggagtcc caagctggct agttaagcta tcaacaagtt tgtacaaaaa agcaggcttt  120
aaaaccatgg tgagcaaggg cgaggagctg ttcaccgggg tggtgcccat cctggtcgag  180
ctggacggcg acgtaaacgg ccacaagttc agcgtgtccg gcgagggcga gggcgatgcc  240
acctacggca agctgaccct gaagttcatc tgcaccaccg gcaagctgcc cgtgccctgg  300
cccaccctcg tgaccacctt cacctacggc gtgcagtgct tcgcccgcta ccccgaccac  360
atgaagcagc acgacttctt caagtccgcc atgcccgaag gctacgtcca ggagcgcacc  420
atcttcttca aggacgacgg caactacaag acccgcgccg aggtgaagtt cgagggcgac  480
accctggtga accgcatcga gctgaagggc atcgacttca aggaggacgg caacatcctg  540
gggcacaagc tggagtacaa ctacaacagc cacaaggtct atatcaccgc cgacaagcag  600
aagaacggca tcaaggtgaa cttcaagacc cgccacaaca tcgaggacgg cagcgtgcag  660
ctcgccgacc actaccagca gaacaccccc atcggcgacg gccccgtgct gctgcccgac  720
aaccactacc tgagcaccca gtccgccctg agcaaagacc ccaacgagaa gcgcgatcac  780
atggtcctgc tggagttcgt gaccgccgcc gggatcactc tcggcatgga cgagctgtac  840
```

```
aagtaagcta agcacttcgt ggccgtcgat cgtttaaagg gaggtagtga gtcgaccagt    900
ggatcctgga ggcttgctga aggctgtatg cgaattcagg acagataaag gcagttttgg    960
ccactgactg actgccttta tgtcctgaat tcaggacaca aggcctgtta ctagcactca   1020
catggaacaa atggcccaga tctggccgca ctcgagatat ctagacccag ctttcttgta   1080
caaagtggtt gatctagagg gccc                                          1104
```